(12) United States Patent
Ohashi et al.

(10) Patent No.: US 7,570,367 B2
(45) Date of Patent: Aug. 4, 2009

(54) OPTICAL INTERFERENCE APPARATUS

(75) Inventors: Mitsuo Ohashi, Yokohama (JP); Yoshitoshi Ito, Ome (JP)

(73) Assignee: Spectratech Inc., Tokyo (JP)

( * ) Notice: Subject to any disclaimer, the term of this patent is extended or adjusted under 35 U.S.C. 154(b) by 390 days.

(21) Appl. No.: 11/620,142

(22) Filed: Jan. 5, 2007

(65) Prior Publication Data
US 2007/0195330 A1 Aug. 23, 2007

(30) Foreign Application Priority Data
Feb. 22, 2006 (JP) ............................. 2006-045629

(51) Int. Cl.
G01B 9/02 (2006.01)
G01B 11/02 (2006.01)
G01J 3/45 (2006.01)
G01J 5/02 (2006.01)

(52) U.S. Cl. ................... 356/511; 356/456; 250/339.08

(58) Field of Classification Search ................. 356/450, 356/451, 489, 495, 496, 498, 511–516; 250/339.07, 250/339.08, 339.09
See application file for complete search history.

(56) References Cited

U.S. PATENT DOCUMENTS

| | | | | | |
|---|---|---|---|---|---|
| 3,668,406 | A | * | 6/1972 | Reid et al. ................... | 356/521 |
| 3,709,610 | A | * | 1/1973 | Kruegle ....................... | 356/635 |
| 4,181,440 | A | * | 1/1980 | Frosch et al. ............... | 356/451 |
| 4,870,648 | A | * | 9/1989 | Ceglio et al. ................ | 372/5 |
| 6,469,790 | B1 | * | 10/2002 | Manning ..................... | 356/451 |
| 7,057,737 | B2 | * | 6/2006 | Millerd et al. .............. | 356/495 |
| 7,095,504 | B1 | * | 8/2006 | Ames et al. .................. | 356/498 |
| 2004/0233459 | A1 | * | 11/2004 | Booth ......................... | 356/498 |
| 2006/0222224 | A1 | * | 10/2006 | Ohashi ........................ | 382/128 |
| 2006/0244972 | A1 | * | 11/2006 | Fercher ....................... | 356/497 |
| 2007/0014464 | A1 | * | 1/2007 | Ohashi ........................ | 382/131 |
| 2007/0195330 | A1 | * | 8/2007 | Ohashi et al. ................ | 356/498 |
| 2009/0027683 | A1 | * | 1/2009 | Suzuki et al. ................ | 356/450 |

FOREIGN PATENT DOCUMENTS

JP 2001-125009 A 5/2001

* cited by examiner

*Primary Examiner*—Patrick J Connolly
(74) *Attorney, Agent, or Firm*—Rossi, Kimms & McDowell, LLP

(57) ABSTRACT

A light emission section includes light generators which are operated on the basis of drive signals from a controller so as to emit near infrared interferable light beams having different specific wavelengths to a light interference section. The light interference section includes a beam splitter having a low-reflection region. The beam splitter allows a most portion of the near infrared interferable light beams to propagate toward an object to be examined, and reflects a portion of the near infrared interferable light beams to a movable mirror. The beam splitter causes interference between measurement light reflected by the object and reference light reflected by the movable mirror, and the resultant interference light propagates to a light detection section. The light detection section receives the interference light and calculates predetermined information regarding the object by making use of the quantity distribution of the interference light. A display section displays the calculated information.

15 Claims, 11 Drawing Sheets

OPTICAL INTERFERENCE APPARATUS

BACKGROUND OF THE INVENTION

1. Field of the Invention

The present invention relates to an optical interference apparatus which obtains, in a non-contacting manner, information regarding an object to be examined by making use of optical interference.

2. Description of the Related Art

Conventionally, optical interference phenomena have been widely utilized for measuring a very small change in distance between objects, the surface shape of an object, or the like. Of various apparatuses utilizing optical interference phenomena, measurement apparatus utilizing a Michelson interferometer, which can readily produce an optical interference phenomenon, are widely known. The Michelson interferometer includes a half mirror or beam splitter which optically splits a light beam into two light beams propagating in two directions. A light beam emitted from a light source is optically split into two light beams by means of the beam splitter disposed on the optical path of the emitted light beam. One of the two light beams reaches an object to be examined, is reflected by the object, and reaches the beam splitter as measurement light. The other light beam is reflected by a reference mirror, and reaches the beam splitter as reference light. Thus, interference light is produced as a result of optical interference between the measurement light and the reference light. Since this interference light changes greatly depending on the state of scatter reflections of the measurement light at the object, the above-described measurement can be performed through observation of the interference light.

As described above, in the Michelson interferometer, various measurements are performed on the basis of generated interference light. Therefore, efficient use of light emitted from the light source, as the measurement light and the reference light, is important. In other words, if the light emitted from the light source cannot be utilized efficiently, measurement accuracy decreases. In general, the beam splitter used in the Michelson interferometer is designed such that the ratio between the quantity of transmitted light and the quantity of reflected light becomes 1:1. Thus, 50% of the light emitted from the light source passes through the beam splitter and reaches the object, and 50% of the emitted light is reflected by the beam splitter and reaches the reflection mirror.

Further, 50% of the measurement light from the object passes through the beam splitter and propagates toward the light source, and 50% of the measurement light is reflected by the beam splitter toward a light detector. Meanwhile, 50% of the reference light from the reference mirror passes through the beam splitter and propagates toward the light detector, and 50% of the reference light is reflected by the beam splitter toward the light source. Accordingly, the respective quantities of the measurement light and reference light actually reaching the light detector are only 25% of the quantity of the light emitted from the light source. Therefore, when the conventional Michelson interferometer configured as described above is used for measurement of an object to be examined, the light emitted from the light source cannot be utilized effectively.

In view of the above, recently, there has been used a Michelson interferometer in which, in order to increase the use efficiency of light, a polarizing beam splitter is used as the beam splitter, and a ¼ λ plate is provided between the beam splitter and an object to be examined and between the beam splitter and the reference mirror. In this improved Michelson interferometer, when a light beam emitted from the light source reaches the polarizing beam splitter, the light is split into two polarized light beams whose polarization planes perpendicularly intersect each other. One polarized light beam passes through the beam splitter, and the other polarized light beam is reflected by the beam splitter. The light beam having passed through the polarizing beam splitter passes through the corresponding ¼ λ plate, and reaches the object. Measurement light from the object passes the ¼ λ plate and reaches the polarizing beam splitter, at which the measurement light has a 90°-rotated polarization plane. Meanwhile, the light beam reflected by the beam splitter passes through the corresponding ¼ λ plate, and reaches the reference mirror. Reference light from the reference mirror passes the ¼ λ plate and reaches the polarizing beam splitter, at which the reference light has a 90°-rotated polarization plane.

Since each of the ¼ λ plates rotates the polarization plane of the corresponding light beam by 90°, the polarizing beam splitter can reflect all (100%) the measurement light, and can pass all (100%) the reference light therethrough. Thus, the respective quantities of the measurement light and reference light reaching the light detector become equal to 50% of the quantity of the light emitted from the light source. Therefore, in the improved Michelson interferometer, the light emitted from the light source can be utilized more effectively. However, even in this case, since only 50% of the light emitted from the light source is used, desire has arisen to use the light more efficiently and improve the measurement accuracy.

Incidentally, in the medical field, use of optical coherence tomography has recently attracted attention, as it facilitates non-invasive measurement of the interior of a living organism. In optical coherence tomography, use of near infrared interferable light attains micron-order imaging of very small regions. Optical coherence tomography has been put into practice particularly in the fields of intracatheters and endoscopes, and Japanese Patent Application Laid-Open (kokai) No. 2001-125009 discloses an endoscope which makes use of a Michelson interferometer. This endoscope enables a physician to view the surfaces of the body cavity wall of a patient by use of visible light or excitation light and to observe the interior of an affected part on the basis of a tomogram obtained by optical coherence tomography using near infrared interferable light, to thereby perform thorough examination. Therefore, cancer, tumor, or other pathological conditions can be detected at an early stage, accurate diagnosis can be made quickly, and stress experienced by patients can be mitigated. As described above, optical coherence tomography achieves accurate and quick diagnosis and reduces stress imposed on patients. Therefore, in recent years, studies for application of this technique to eye diseases have been actively carried out.

However, although the endoscope disclosed in the above-mentioned publication enables a physician to obtain a tomogram of an affected part, the information the physician can obtain is limited to only that regarding the profile obtained from the tomogram. Therefore, in diagnosis of a patient in terms of pathological condition and development, the physician must rely on his experience and knowledge, thereby increasing the burden imposed on the physician. In diagnosis of eye diseases, particularly an eye disease in the vicinity of the retina of the eyeball, observation of a very small area is required, thereby further increasing the burden imposed on the eye doctor. Moreover, in an eye disease involving necrosis of photoreceptor cells, such as glaucoma, accurate diagnosis may be difficult to perform on the basis of only the information regarding the profile obtained from a tomogram. Therefore, particularly in diagnosis of eye diseases, there has been keen demand for a practical measuring apparatus which makes use of optical coherence tomography and which can provide eye doctors with a greater deal of accurate information.

However, when a greater quantity of accurate information is to be provided through measurement, it is necessary to emit near-infrared interferable light beams having different wavelengths, and to detect and measure a plurality of beams of measurement light (near-infrared interferable light) from the object. In this case, for example, when the above-described improved Michelson interferometer is employed, the optical system may become complex. That is, the characteristics of an optical system composed of a polarizing beam splitter and ¼ λ plates change depending on the wavelength of incoming light (near infrared interferable light) (so called wavelength dependency). Therefore, when multi-wavelength, near-infrared interferable light is used, an optical system composed of a polarizing beam splitter and ¼ λ plates must be provided for each wavelength. In this case, the optical path from the light source to an object to be examined becomes complex, whereby adjustment for securing a proper optical path becomes extremely difficult, and thus, the adjustment work may become troublesome. In addition, because of the increased complexity of the optical system, the apparatus itself becomes larger, which is not practical.

SUMMARY OF THE INVENTION

The present invention has been accomplished to solve the aforementioned problems. An object of the present invention is to provide an optical interference apparatus in which light is used more efficiently for measurement of an object to be examined and in which the configuration of the optical system is simplified through elimination of wavelength dependency.

The present invention provides an optical interference apparatus comprises a controller, a light emission section, a light interference section, and a light detection section. The controller is operable by a user and outputs various signals on the basis of instructions from the user. The light emission section includes a light source for emitting light on the basis of a predetermined drive signal supplied from the controller and adapted to emit a beam of light having a specific wavelength. The light interference section includes splitting means having a low-reflection region for permitting the greater portion of the light beam emitted from the light emission section to pass therethrough toward an object to be examined, a portion of the emitted light beam being reflected and optically separated at the low-reflection region; reflection means for reflecting toward the splitting means the portion of the light beam reflected and separated at the low-reflection region of the splitting means; moving means for moving the reflection means along the optical axis of the light beam separated through reflection; and light interference means for causing optical interference between the light beam reflected by the reflection means and the light beam reflected by the object to be examined. The light detection section includes light-receiving means for receiving interference light produced as a result of the optical interference at the light interference section. In this case, the splitting means of the light interference section is composed of a substrate formed of a transparent material, a reflection layer formed on one side of the substrate, and a transmission hole formed in the reflection layer so as to permit passage therethrough of the greater portion of the light beam emitted from the light emission section. Further, in order to prevent deterioration of the reflection layer, the splitting means of the light interference section preferably includes a protection layer formed on the reflection layer so as to prevent deterioration of the reflection layer, and a reflection suppression layer formed on the other side of the substrate and suppressing reflection of the light beam propagating from the light emission section.

The optical interference apparatus according to the present invention operates as follows. That is, when a user operates the controller, the light source of the light emission section emits a light beam having a specific wavelength. The light interference section optically divides the light beam emitted from the light emission section by means of the splitting means. Since the splitting means is configured such that a transmission hole is formed in the reflection layer layered on the substrate formed of a transparent material, the portion where the transmission hole is formed serves as the low reflection region. Therefore, the light beam emitted from the light emission section passes through the substrate and the transmission hole of the splitting means, whereby the greater portion of the emitted light beam propagates toward the object to be examined. This light beam is reflected by the object, and propagates toward the splitting means. Meanwhile, a portion of the light beam emitted from the light emission section is reflected at the low reflection region toward the reflection means, and the light beam reflected by the reflection means propagates toward the splitting means.

These light beams having reached the splitting means propagate toward the light-receiving means of the light detection section. That is, since the light beam reflected by the object reaches the splitting means with the beam expanded, the greater portion of the reflected light beam is reflected by the reflection layer of the splitter to propagate toward the light detection section. Meanwhile, the greater portion of the light beam reflected by the reflection means passes through the substrate and transmission hole of the splitting means, and propagates toward the light detection section. Thus, the greater portion of the light emitted from the light emission section causes optical interference. The interference light produced as a result of the optical interference is received by the light-receiving means of the light detection section. In this case, if the protection layer is formed on the reflection layer, over a long period of time, the reflection layer can reflect well the light beam reflected by the object. Meanwhile, if the reflection suppression layer is formed on the substrate, useless reflection of the light having reached the splitting means can be suppressed.

Accordingly, in the optical interference apparatus according to the present invention, the light emitted from the light emission section can be used quite efficiently for measurement. As a result, measurement accuracy can be increased. In addition, since the splitting means of the light interference section does not polarize the light propagating from the light emission section, provision of a ¼ λ plate having a wavelength dependency is not required. Therefore, the configuration of the optical system of the optical interference apparatus can be simplified through elimination of the wavelength dependency, and operations required for measurement, such as setting the optical axis, can be performed quite easily.

According to another feature of the present invention, the light emission section includes a plurality of light sources for emitting near infrared interferable light on the basis of predetermined drive signals supplied from the controller and adapted to emit near infrared interferable light beams having different specific wavelengths; and the light detection section includes light-receiving means for receiving interference light including the near infrared interferable light beams emitted from the light emission section and having different specific wavelengths.

In this case, preferably, the light emission section further includes spread spectrum modulation means for modulating predetermined primary drive signals supplied from the controller by spread spectrum modulation to thereby generate secondary drive signals, and light-mixing means for optically mixing the near infrared interferable light beams having different specific wavelengths simultaneously emitted from the light sources driven simultaneously on the basis of the secondary drive signals; and the light detection section further includes demodulation means for despreading and demodulating the secondary drive signals contained in the interference light rays received by the light-receiving means to thereby obtain the predetermined primary drive signals. Alternatively, the light emission section further includes frequency-division-multiple-access-modulation means for modulating predetermined primary drive signals supplied from the controller by means of frequency division multiple-access modulation to thereby generate secondary drive signals, and light-mixing means for optically mixing the near infrared interferable light beams having different specific wavelengths simultaneously emitted from the light sources driven simultaneously on the basis of the secondary drive signals; and the light detection section further includes demodulation means for demodulating the secondary drive signals contained in the interference light rays received by the light-receiving means to thereby obtain the predetermined primary drive signals.

Moreover, preferably, the light emission section acquires predetermined drive signals supplied from the controller with a predetermined time interval therebetween, and the light sources are successively driven on the basis of the acquired predetermined drive signals so as to successively emit near infrared interferable light beams having different specific wavelengths with the predetermined time interval therebetween. In this case, preferably, the light emission section further includes spread spectrum modulation means for modulating, by spread spectrum modulation, predetermined drive signals supplied from the controller with the predetermined time interval therebetween to thereby generate modulated drive signals, whereby the light sources are successively driven by the modulated drive signals so as to successively emit near infrared interferable light beams having different specific wavelengths with the predetermined time interval therebetween; and the light detection section further includes demodulation means for demodulating the modulated drive signals contained in the interference light rays received by the light receiving means to thereby obtain the predetermined drive signals. Alternatively, the light emission section further includes modulation means for modulating, by means of frequency division multiple-access modulation, predetermined drive signals supplied from the controller with the predetermined time interval therebetween to thereby generate modulated drive signals, whereby the light sources are successively driven by the modulated drive signals so as to successively emit near infrared interferable light beams having different specific wavelengths with the predetermined time interval therebetween; and the light detection section further includes demodulation means for demodulating the modulated drive signals contained in the interference light rays received by the light receiving means to thereby obtain the predetermined drive signals.

By virtue of these configurations, the light emission section can emit a plurality of near infrared interferable light beams having specific wavelengths simultaneously or successively. In the case where the plurality of near infrared interferable light beams having specific wavelengths are output simultaneously, the light sources can be driven on the basis of the secondary drive signals, which are obtained by modulating the primary drive signals from the controller by spread spectrum modulation or frequency division multiple-access modulation. Further, the light detection section can receives interference light of the emitted near infrared interferable light beam by means of the light-receiving means composed of, for example, a photoelectric conversion element, and demodulate the secondary drive signals contained in the received interference light to thereby detect the primary drive signals. In this manner, the optical interference apparatus can measure an object to be examined by use of multi-wavelength near infrared interferable light. Further, even when the light interference section causes interference among the near infrared interferable light beams having specific wavelengths, as described above, the light interference section can employ a simplified optical system configuration through elimination of wavelength dependency. Accordingly, the light emitted from the light emission section can be utilized quite efficiently for measurement, and as a result, measurement accuracy can be enhanced.

In the case where a plurality of near infrared interferable light beams having different specific wavelengths are successively emitted with a predetermined time interval therebetween, the detection speed required for the light-receiving means (e.g., photo detector) of the light detection section can be decreased, so that the production cost of the optical interference apparatus can be lowered.

According to another feature of the present invention, the light detection section further comprises calculation means for calculating predetermined information regarding the object on the basis of the light quantities of the interference light rays received by the light-receiving means. In this case, preferably, the light detection section further comprises a display section including image data generation means for generating visible image data on the basis of the predetermined information regarding the object calculated by the calculation means and display means for displaying an image on the basis of the image data generated by the image data generation means. In this case, preferably, the object to be examined is a living organism, and the calculation means of the light detection section is composed of profile information calculation means for calculating profile information representing the profile of the object on the basis of the light quantities of the interference light rays received by the light-receiving means, and biological information calculation means for calculating biological information of the object associated with metabolism of the living organism on the basis of the light quantities of the near infrared interferable light beams emitted from the light emission section and the light quantities of the interference light rays received by the light-receiving means. The biological information calculated by the biological information calculation means may be one selected from the group consisting of blood volume, blood flow rate, change in blood flow, and the degree of oxygen saturation (hereinafter simply referred to as "oxygen saturation") within a blood vessel of the living organism. Moreover, the living organism may be the eyeground of the eyeball.

By virtue of these configurations, upon receipt of interference light by the light-receiving means, the calculation means of the light detection section can calculate the predetermined information regarding the object on the basis of the quantity of the received interference light. Thus, the display section can display the calculated information regarding the object in a visible manner.

When the object to be examined is a living organism, a larger number of pieces of accurate information can be measured through simultaneous or successive emission of a plurality of near infrared interferable light beam from the light emission section, whereby a larger number of pieces of accurate information can be provided to a medical doctor or the like. That is, in this case, the light detection section receives interference light, calculates profile information representing the profile of the object on the basis of the light quantities of the received interference light rays, and calculates biological information of the object, such as blood volume, blood flow rate, change in blood flow, and oxygen saturation, on the basis of the light quantity of the near infrared interferable light beam emitted from the light emission section and the light quantity of the received interference light. Further, the display section generates visible image data on the basis of the calculated profile information and the calculated biological information. The display section displays a profile image based on the calculated profile information, a biological information image based on the calculated biological information, or a composite image obtained through composition of the profile image and the biological information image. Accordingly, a large number of pieces of information can be provided to a medical doctor or the like. At this time, preferably, the display section displays a composite image obtained by mixing the profile image and the biological information image such that a position specified by the profile image of the object and a position specified by the biological information image of the object coincide with each other.

In particular, when a medical doctor observes a region by use of a displayed image representing the profile, an image representing the biological information of a region corresponding to the region can be displayed while mixing (superimposing) the biological information image with the profile image. By virtue of this, a medical doctor can diagnose pathological condition and development considerably easily and accurately. Moreover, since blood volume, blood flow rate, change in blood flow, oxygen saturation, etc. can be easily calculated and displayed as biological information necessary for diagnosis of pathology, pathological condition and development can be diagnosed considerably easily and accurately. In addition, since the light emission section includes a plurality of light sources and can emit near infrared interferable light beams having different specific wavelengths, for calculation of biological information, the light emission section can selectively emit a near infrared interferable light beam having a suitable wavelength. This enables more accurate calculation of biological information, and assists a medical doctor's diagnosis more properly.

When the object to be examined is a living organism, the following effect can be achieved through simultaneous emission of a plurality of near infrared interferable light beams. That is, for example, when oxygen concentration within the artery or arteriole is calculated, the oxygen concentration must be calculated on the basis of the quantity of interference light stemming from a pulse wave of the blood flow. At this time, since the state of the pulse wave changes at extremely high speed, in the case where near infrared interferable light beams are successively emitted, the quantities of interference light rays detected by the light detection section for the near infrared interferable light beams represent different states of the pulse wave. Therefore, the calculated biological information may be of poor accuracy. In contrast, in the case where near infrared interferable light beams are simultaneously emitted, the quantities of interference light rays detected by the light detection section represent substantially the same state of the pulse wave. Therefore, the biological information can be calculated accurately, and a medical doctor's diagnosis can be assisted more properly.

Moreover, another feature of the present invention resides in that a light separation section for optically separating interference light rays produced as a result of optical interference at the light interference section is provided between the light interference section and the light detection section, and the light detection section includes a plurality of right-receiving means for receiving the interference light rays separated by the light separation section. By virtue of this configuration, even when near infrared interferable light beams having different specific wavelengths are simultaneously emitted from the light emission section, resultant interference light rays can be optically separated by the light separation section (e.g., a dichroic mirror or a half mirror). Therefore, the structure of the optical interference apparatus can be simplified.

BRIEF DESCRIPTION OF THE DRAWINGS

Various other objects, features, and many of the attendant advantages of the present invention will be readily appreciated as the same becomes better understood with reference to the following detailed description of the preferred embodiments when considered in connection with the FIG. 1 is a block diagram schematically showing a optical interference apparatus according to first and second embodiments of the present invention.

DETAILED DESCRIPTION OF PREFERRED EMBODIMENTS a. First Embodiment

Figure 1:
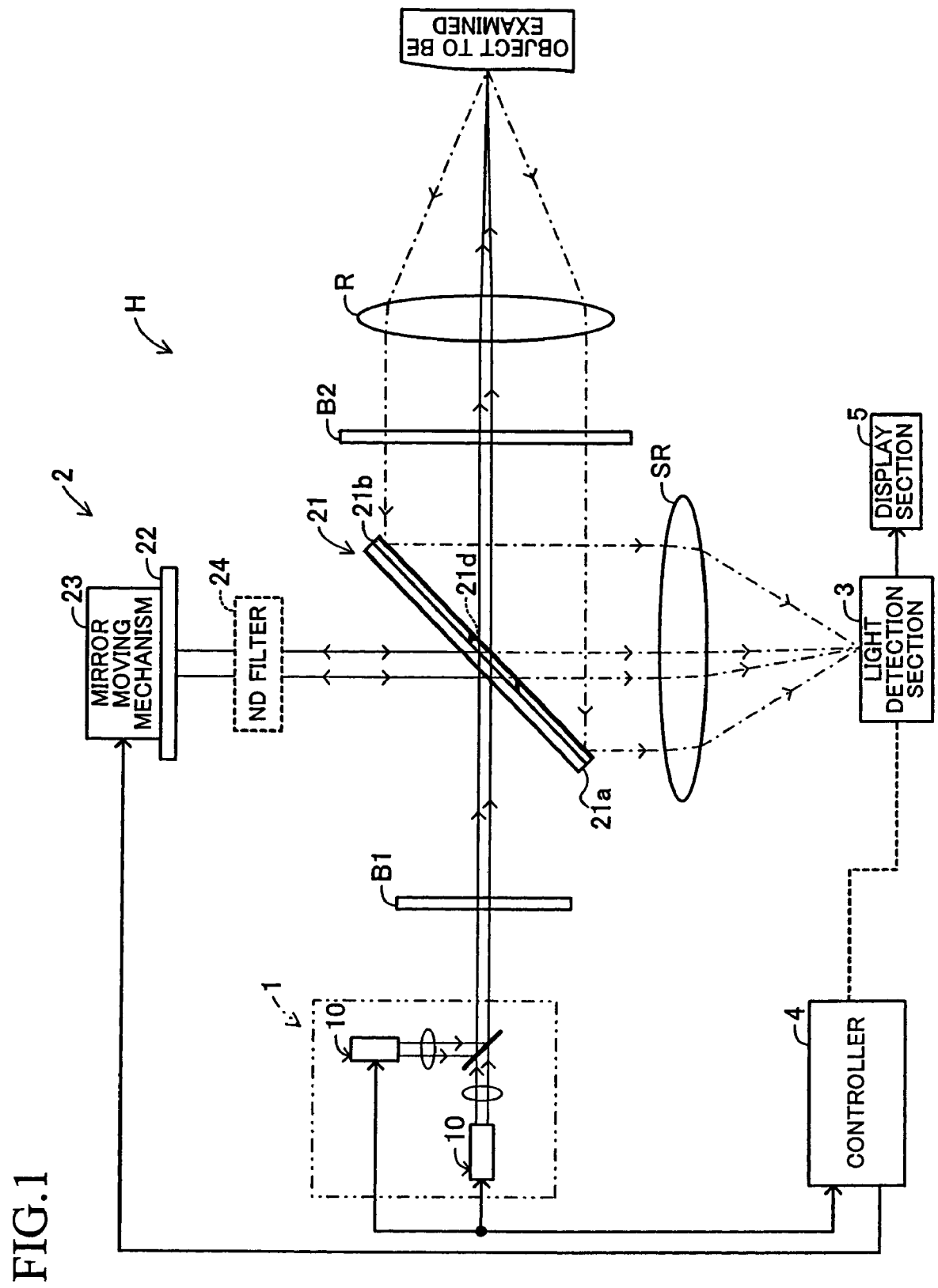

A first embodiment of the present invention will next be described with reference to the drawings. FIG. 1 schematically shows the configuration of an optical interference apparatus H according to the present embodiment. As shown in FIG. 1, the optical interference apparatus H includes a light emission section 1, a light interference section 2, and a light detection section 3. The optical interference apparatus H also includes a controller 4, which is mainly composed of a microcomputer including a CPU, ROM, RAM, etc.

The light emission section 1 is composed of a plurality of light generators 10 which generate light beams having different specific wavelengths. In the present embodiment, as shown in FIG. 1, the light emission section 1 is composed of two light generators 10; that is, the light emission section 1 generates light beams having two specific wavelengths. However, no restriction is imposed on the number of the light generators 10 of the light emission section 1; i.e., the number of specific wavelengths of the emitted light. For example, the light emission section 1 may be configured to include three or more light generators 10. If necessary, through provision of a large number of light generators 10, high detection accuracy of the optical interference apparatus H can be secured.

Figure 2:
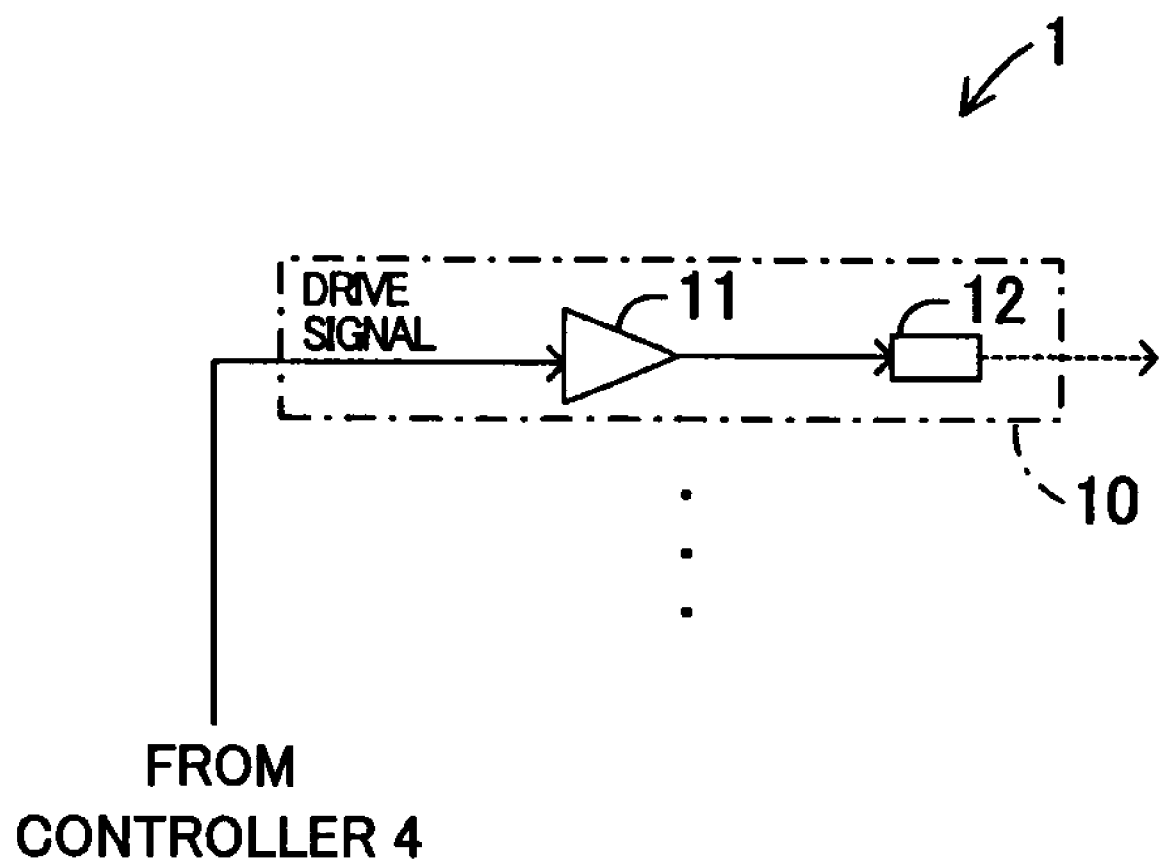
FIG. 2 is a block diagram schematically showing the configuration of a light emission section shown in FIG. 1.

As shown in FIG. 2, each light generator 10 includes a light source driver 11 for acquiring or obtaining a drive signal supplied from the controller 4. On the basis of the drive signal obtained from the controller 4, the light source driver 11 drives a light source 12. The light source 12 may be composed of a light-emitting element capable of any type. In the following description of the present embodiment, the light source 12 is assumed to be composed of a near-infrared light-emitting element such as a laser diode (LD) or a super luminescent diode (SLD). Thus, since the light source 12 is composed of a near-infrared light-emitting element, the light source 12 can emit near-infrared interferable light of a specific wavelength having coherence of a certain degree or greater.

The specific wavelength of the near-infrared interferable light emitted by the light source 12 is preferably determined to fall within a range of 600 nm to 900 nm, for example. The following description is based on the assumption that one light source 12 emits near-infrared interferable light having a specific wavelength of 780 nm, and the other light source 12 emits near-infrared interferable light having a specific wavelength of 830 nm.

As shown in FIG. 1, the near-infrared interferable light emitted by each light source 12 is regulated by means of a collimate lens to have parallel rays, and a resultant near-infrared interferable light beam is caused to travel along a common optical axis by means of a half mirror. The near-infrared interferable light beam emitted in this manner passes through a polarization plate B1 where the near-infrared interferable light beam is subjected to linear polarization, and then propagates to the light interference section 2. Notably, when the above-mentioned LD or SLD is employed as the light source 12, since the emitted near-infrared interferable light has a specific polarization plane, the polarization plate B1 may be omitted.

The light interference section 2 divides the near-infrared interferable light beam emitted from the light emission section 1 into two light beams propagating in two directions, and causes interference between corresponding reflection light beams of the two near-infrared interferable light beams. For such a purpose, as shown in FIG. 1, the light interference section 2 includes a beam splitter 21, a movable mirror 22, and a mirror-moving mechanism 23.

Figure 3:
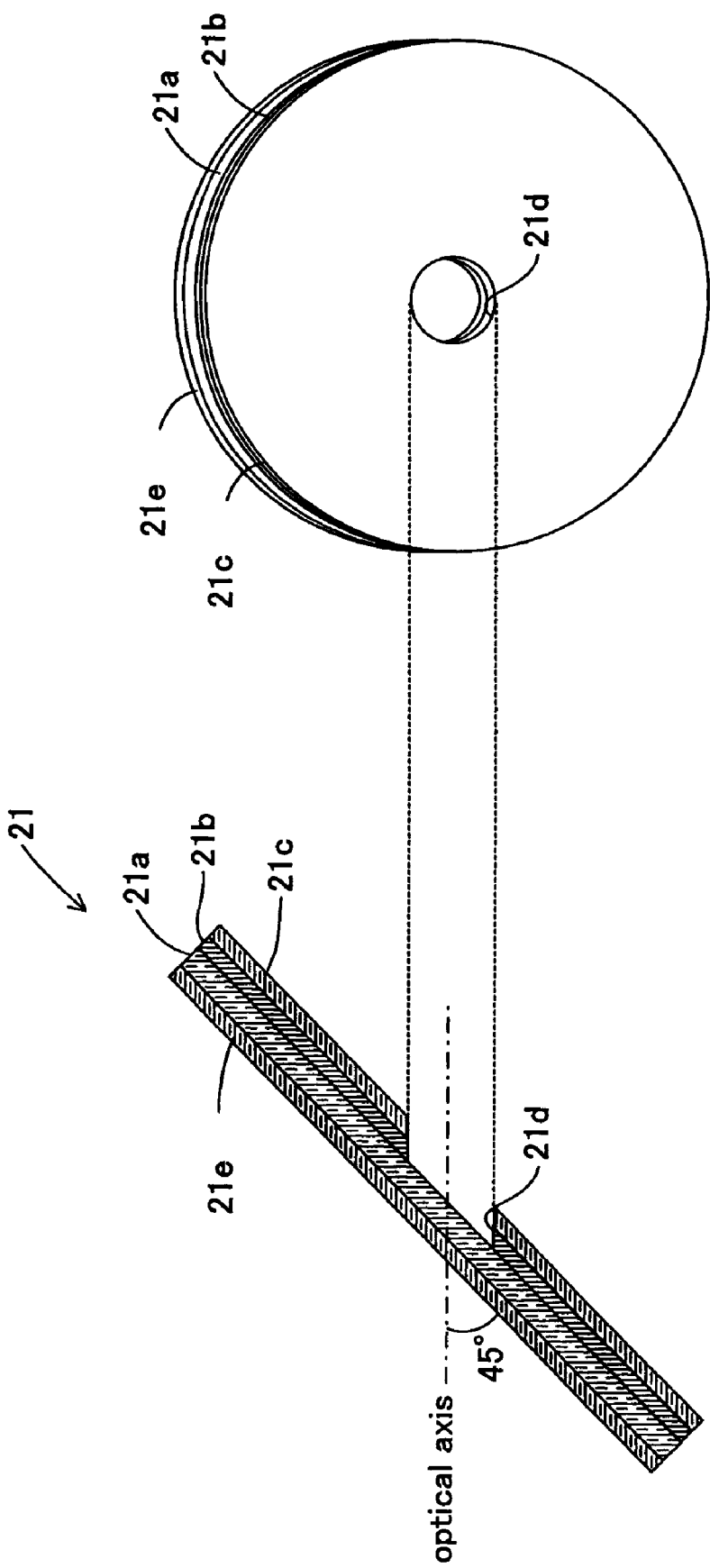
FIG. 3 is a schematic view showing the structure of a beam splitter of a light interference section shown in FIG. 1.

As shown in FIG. 3, the beam splitter 21 includes a substrate 21a formed from a transparent material having a low index of refraction such as borosilicate glass (trade name: BK7) or fused quartz glass (trade name: Quartz). Notably, the substrate 21a preferably has a thickness of about 0.3 mm. An aluminum deposition film 21b having a predetermined thickness (e.g., about 0.1 μm) is formed as a reflection layer on one side of the substrate 21a; more specifically, on the side facing an object to be examined. A protection layer 21c for preventing oxidation of the aluminum deposition film 21b is formed on the aluminum deposition film 21b. Notably, $SiO_2$, SiO, $Al_2O_3$, or any other suitable material is used to form the protection layer 21c.

A portion where the layers are not formed; i.e., a hole portion 21d (hereinafter called transmission hole 21d) is formed generally at the center (as viewed in a plane along which the layers 21b and 21c are formed) of the aluminum deposition film 21b and the protection layer 21c, which form the beam splitter 21. The transmission hole 21d is preferably formed by a method in which a portion of the substrate 21a corresponding to the transmission hole 21d is covered with a mask when the aluminum deposition film 21b and the protection layer 21c are formed, or a method in which after the aluminum deposition film 21b and the protection layer 21c are formed, portions of the aluminum deposition film 21b and the protection layer 21c corresponding to the transmission hole 21d are removed by means of etching.

The transmission hole 21d is formed such that, in a state in which the beam splitter 21 is disposed in the optical interference apparatus H; specifically, the beam splitter 21 is disposed with an inclination of 45° with respect to the optical axis of the near-infrared interferable light beam emitted from the light emission section 1, the transmission hole 21d assumes a circular shape having a predetermined diameter as viewed from the object to be examined. No particular limitation is imposed on the predetermined diameter; however, the predetermined diameter is preferably equal to or greater than that of the near-infrared interferable light beam emitted from the light emission section 1. Further, no particular limitation is imposed on the shape of the transmission hole 21d, and the transmission hole 21d may assume any shape other than a completely circular shape, such as an elongated shape or a rectangular shape. Notably, a region of the substrate 21a corresponding to the transmission hole 21d forms a low-reflection region according to the present invention.

A reflection-suppressing layer 21e is formed on the other side of the substrate 21a; specifically, the side facing the light source 12. This reflection-suppressing layer 21e prevents the near-infrared interferable light beam having reached the beam splitter 21 from being reflected at the light source 12 side surface of the substrate 21a and propagating toward the movable mirror 22, and allows the near-infrared interferable light beam to be reflected at the inner surface of the substrate 21a located on the side toward the object (i.e., the interface between the substrate 21a and air) and propagate toward the movable mirror 22. Preferably, the reflection-suppressing layer 21e is formed from magnesium fluoride. In the present embodiment, the beam splitter 21 assumes a circular shape as shown in FIG. 3; however, the beam splitter 21 may assume any other shape such as a rectangular shape.

The beam splitter 21 formed as described above allows the greater portion of the near-infrared interferable light beam emitted from the light emission section 1 to pass therethrough and propagate toward the object, and reflects a portion of the near-infrared interferable light beam toward the movable mirror 22, to thereby split the incoming near-infrared interferable light beam into two beams propagating in two directions. The splitting of the near-infrared interferable light beam by the beam splitter 21 will be described with reference to FIGS. 1 and 3. The near-infrared interferable light beam emitted from the light source 12 passes through the reflection suppression layer 21e and reaches the substrate 21a. When the near-infrared interferable light beam enters the substrate 21a, because of the presence of the transmission hole 21d formed as described above, the greater portion (about 96%) of the near-infrared interferable light beam passes toward the object without being reflected.

However, when the near-infrared interferable light beam enters the substrate 21a, it is reflected by the inner surface of the substrate 21a located on the side toward the object (i.e., the interface between the substrate 21a and air). Therefore, when the near-infrared interferable light beam passes through the substrate 21a, a portion (about 4%) of the near-infrared interferable light beam is reflected and propagates toward the movable mirror 22. Notably, the near-infrared interferable light beam having passed through the beam splitter 21 propagates toward the object via, for example, an optical fiber. Further, the near-infrared interferable light beam reflected by the beam splitter 21 propagates toward the movable mirror 22 via, for example, an optical fiber.

As shown in FIG. 1, the movable mirror 22 is disposed in such a manner that its reflection surface perpendicularly intersects the optical axis of the near-infrared interferable light beam reflected by the beam splitter 21. By virtue of this arrangement, the movable mirror 22 reflects the near-infrared interferable light beam reflected by the beam splitter 21 to propagate toward the beam splitter 21 along the same optical axis. The mirror-moving mechanism 23 is an actuator including, for example, a piezoelectric element as a main component. The mirror-moving mechanism 23 is controlled by the controller 4 so as to move the movable mirror 22 along the optical axis of the near-infrared interferable light beam reflected by the beam splitter 21.

Next, operation of the light interference section 2 having the above-described configuration will be described with reference to FIG. 1. The near-infrared interferable light beam output from the light emission section 1 reaches the beam splitter 21. Notably, in the case where the near-infrared interferable light beam is emitted from a light source other than a near infrared light emitting element such as LD or SLD, the near-infrared interferable light beam reaches the beam splitter 21 after being subjected to linear polarization at the polarization plate B1. As described above, the greater portion of the near-infrared interferable light beam having reached the beam splitter 21 passes through the substrate 21*a* and the transmission hole 21*d*, and passes through a polarization plate B2 via an unillustrated optical fiber. In the case where an LD or SLD is used for the light source 12, the direction of linear polarization of the polarization plate B2 is adjusted such that the direction of linear polarization coincides with the polarization plane of the near-infrared interferable light beam emitted from these elements. Thus, the near-infrared interferable light beam having passed through the beam splitter 21 passes through the polarization plate B2 as is. Notably, in the case where the polarization plate B1 is provided, if the direction of linear polarization of the polarization plate B1 is rendered coincident with that of the polarization plate B2, the near-infrared interferable light beam having passed through the beam splitter 21 passes through the polarization plate B2 as is. The near-infrared interferable light beam having passed through the polarization plate B2 in this manner is converged by means of an objective lens R, and reaches the object. In this case, preferably, the optical interference apparatus H is configured such that the optical axis of the near-infrared interferable light beam having passed through the polarization plate B2 is changed by use of, for example, an unillustrated 2-axis galvanometer mirror so as to move the focus formed by the objective lens R for scanning the object.

The near-infrared interferable light beam converged by the objective lens R is reflected by the object as indicated by chain lines. In the following description, the near-infrared interferable light beam reflected by the object will be referred to as measurement light. The measurement light greatly scatters because of reflection by the object. In other words, the measurement light forms a greatly expanded beam. The greatly expanded measurement light beam is regulated to have parallel rays upon passage through the objective lens R, and then passes through the polarization plate B2. Since the direction of linear polarization of the polarization plate B2 coincides with the polarization plane of the near-infrared interferable light beam emitted from the light source 12 (or the direction of linear polarization of the polarization plate B1), the polarization plane of the measurement light beam having passed through the polarization plate B2 coincides with that of the near-infrared interferable light beam having passed through the beam splitter 21. When the measurement light beam having passed through the polarization plate B2 reaches the beam splitter 21, it is reflected by the aluminum deposition layer 21*b*. Since the measurement light beam has been expanded greatly, the greater portion of the measurement light beam having reached the beam splitter 21 changes its propagation direction by 90° so as to propagate toward the light detection section 3.

As in the case of passage of the near-infrared interferable light beam, a portion (about 4%) of the measurement light beam passing through the transmission hole 21*d* and the substrate 21*a* is reflected when it passes through the substrate 21*a*. Further, the opening area of the transmission hole 21*d* is smaller than the reflection area of the aluminum deposition layer 21*b*, and the quantity of the measurement light passing through the transmission hole 21*d* and the substrate 21*a* is small. Therefore, passage of the measurement light through the transmission hole 21*d* and the substrate 21*a* exerts a considerably small influence on measurement accuracy.

Meanwhile, the near-infrared interferable light beam propagating from the beam splitter 21 toward the movable mirror 22 reaches the movable mirror 22 via an unillustrated optical fiber. The near-infrared interferable light beam reflected by the movable mirror 22 reaches the beam splitter 21 via the same optical fiber. In the following description, the near-infrared interferable light beam reflected by the movable mirror 22 will be referred to as reference light. As in the case of passage of the near-infrared interferable light beam, the greater portion (about 96%) of the reference light beam having reached the beam splitter 21 passes through the transmission hole 21*d* and the substrate 21*a*, and propagates toward the light detection section 3. Notably, although a portion (about 4%) of the reference light beam is reflected toward the light emission section 1 when it passes through the substrate 21*a*, the influence on the measurement accuracy is very small, because the quantity of the reflected reference light is small.

The polarization plane of the reference light beam is maintained to coincide with the polarization plane of the near-infrared interferable light beam emitted from the light source 12 (or the polarization plane of the beam after being subjected to linear polarization performed by the polarization plate B1). Therefore, the polarization plane of the measurement light reflected by the beam splitter 21 and propagating toward the light detection section 3 coincides with that of the reference light passing through the beam splitter 21 and propagating toward the light detection section 3. As a result, the measurement light and the reference light interfere with each other. In the following description, light produced as a result of interference between the measurement light and the reference light will be referred to as interference light. This interference light is caused to propagate through an unillustrated fiber or the like and is detected by the light detection section 3 after being converged by means of a condenser lens SR.

Figure 4:
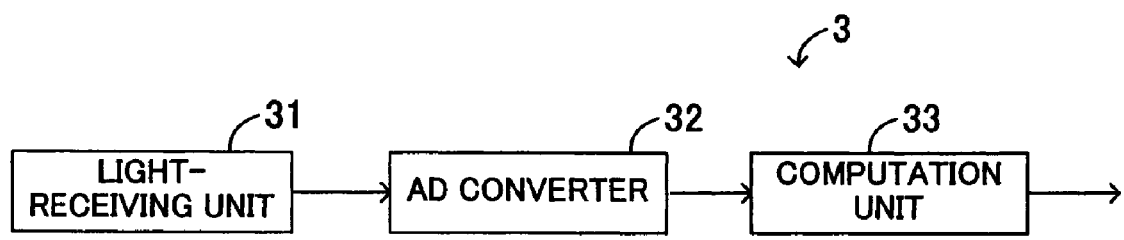
FIG. 4 is a block diagram schematically showing the configuration of a light detection section shown in FIG. 1.

The light detection section 3 detects the interference light from the light interference section 2, and uses a detection signal corresponding to the detected interference light so as to output information regarding the object (e.g., a cross sectional shape or blood oxygen saturation of a living organism to be described later, a very small change in distance between objects, a surface shape of an object, or the like). For such a purpose, as shown in FIG. 4, the light detection section 3 includes a light-receiving unit 31, an AD converter 32, and a computation unit 33. The light-receiving unit 31 is mainly composed of a photoelectric conversion element such as a photo detector or a photo diode. Upon receipt of interference light from the light interference section 2, the light-receiving unit 31 outputs to the AD converter 32, in a time series fashion, an electrical detection signal representing the quantity of the interference light, for example. The AD converter 32 converts the electrical detection signal (analog signal) output from the light-receiving unit 31 to a digital signal, and outputs the digital signal to the computation unit 33.

The computation unit 33 is mainly composed of a CPU, ROM, RAM, etc. The computation unit 33 obtains information regarding the object through calculation on the basis of the detection signal (digital signal) output from the AD converter 32. As will be exemplified later, the obtainment of the information by the computation unit 33 through calculation will be specifically described for the case where the optical interference apparatus H is applied to observation of the eyeground.

Figure 5:
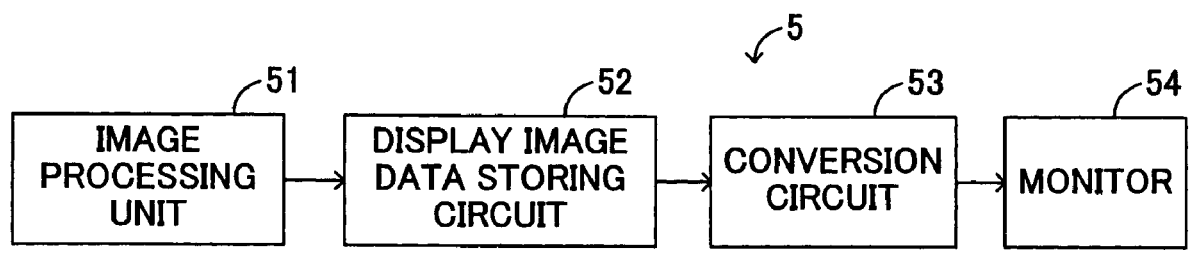
FIG. 5 is a block diagram schematically showing the configuration of a display section shown in FIG. 1.

As shown in FIG. 1, the optical interference apparatus H further comprises a display section 5. As shown in FIG. 5, the display section 5 includes an image-processing unit 51, a display image data storage circuit 52, a conversion circuit 53, and a monitor 54.

Figure 6:
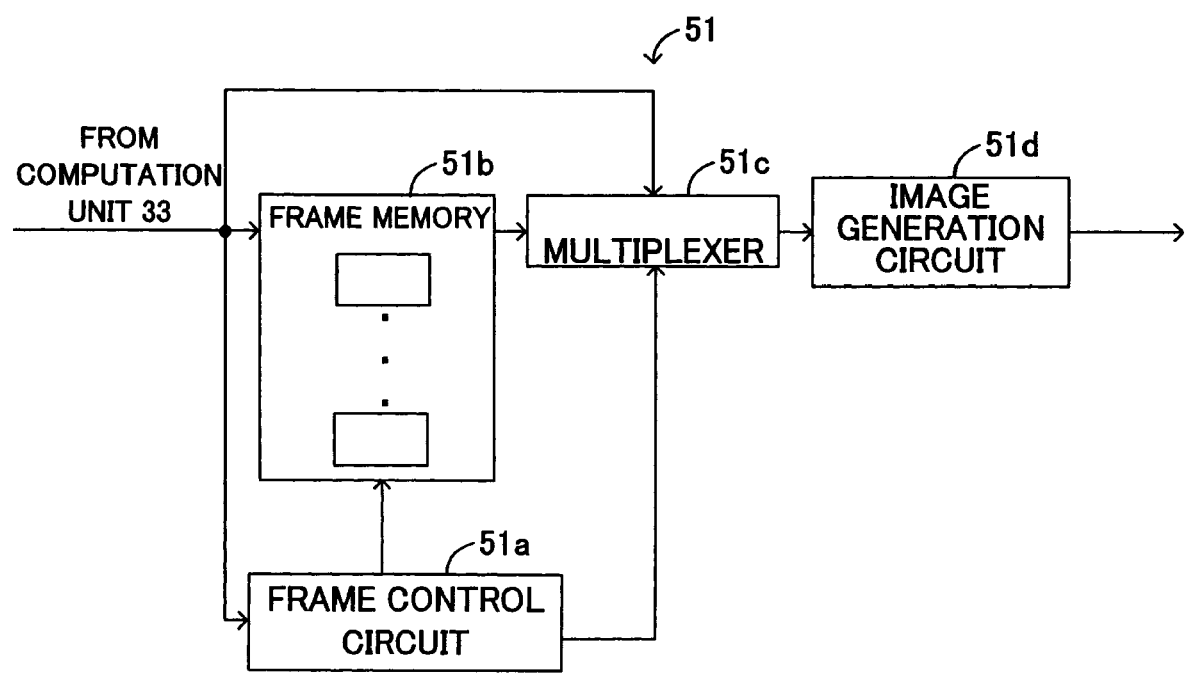
FIG. 6 is a block diagram schematically showing the configuration of an image processing unit shown in FIG. 5.

As shown in FIG. 6, the image-processing unit 51 includes a frame control circuit 51*a*, frame memories 51*b*, a multiplexer 51*c*, and an image generation circuit 51*d*. The frame control circuit 51*a* controls operations of the frame memories 51*b* and the multiplexer 51*c*. Under the control by the frame control circuit 51*a*, the frame memories 51*b* output to the image generation circuit 51*d* the signal which is output from the computation unit 33 of the light detection section 3 and represents the information regarding the object. The image generation circuit 51*d* generates image data on the basis of the output signal in a predetermined manner. In the present embodiment, the signal output from the computation unit 33 is temporarily stored in the frame memories 51*b*. However, if necessary, these signals may be output directly to the multiplexer 51*c*.

The display image data storage circuit 52 temporarily stores the image data, while superposing additional data (information), such as numerals and various characters, on the image data, when necessary. The conversion circuit 53 performs, for example, D/A conversion and video format conversion for the image data stored in the display image data storage circuit 52.

Next, operation of the optical interference apparatus H having the above-described configuration will be described, by reference to an example case where the eyeground of a patient is observed for diagnosis of eye disease.

A medical doctor or operator places the optical interference apparatus H such that the eyeball of the patient (object to be examined) is located on the optical axis of the near-infrared interferable light beam output from the light emission section 1. At this time, since the optical system of the optical interference apparatus H has a simplified structure as described above, the medical doctor or operator can place the optical interference apparatus H while adjusting the optical axis quite easily. The medical doctor or operator then operates an unillustrated input unit of the controller 4 to thereby instruct start of output of the near-infrared interferable light beam. In response thereto, the controller 4 supplies, at predetermined, short intervals, to the two light generators 10 of the light emission section 1, respective drive signals for driving the light generators 10 to thereby emit near-infrared interferable light beams. Thus, the two light generators 10 alternately start their operations at predetermined, short intervals.

That is, in the light generator 10 for emitting a near-infrared interferable light beam of 780 nm, the light source driver 11 receives the drive signal supplied from the controller 4 at predetermined, short intervals. As a result, on the basis of the received drive signal, the light source driver 11 causes the light source 12 to emit an optical pulse, whereby a near-infrared interferable light beam of 780 nm is output from the light source 12 toward the half mirror via the corresponding collimate lens. Similarly, in the light generator 10 for emitting a near-infrared interferable light beam of 830 nm, the light source driver 11 receives the drive signal supplied from the controller 4 at predetermined, short intervals. As a result, on the basis of the received drive signal, the light source driver 11 causes the light source 12 to emit an optical pulse, whereby a near-infrared interferable light beam of 830 nm is output from the light source 12 toward the half mirror via the corresponding collimate lens. In this manner, the near-infrared interferable light beams emitted from the light sources 12 pass through the half mirror, and then propagate toward the light interference section 2 along the common optical axis. In the following description, the two near-infrared interferable light beams will be collectively referred to as a near-infrared interferable light beam.

The near-infrared interferable light beam having reached the light interference section 2 is optically divided into two beams by means of the beam splitter 21. That is, the greater portion of the near-infrared interferable light beam propagates through the reflection suppression layer 21*e*, the substrate 21*a*, and the transmission hole 21*d*; passes through the polarization plate B2 and the objective lens R; and reaches the eyeball of the patient. In the following description, the near-infrared interferable light beam that reaches the eyeball of the patient will be referred to as the first near-infrared interferable light beam. Further, a portion of the near-infrared interferable light beam having reached the beam splitter 21 propagates through the reflection suppression layer 21*e*, is reflected and scattered within the substrate 21*a*, and reaches the movable mirror 22. In the following description, the near-infrared interferable light beam that reaches the movable mirror 22 will be referred to as the second near-infrared interferable light beam.

The first near-infrared interferable light beam having reached the eyeball is reflected and scattered at the eyeground. The reflected first near-infrared interferable light, which serves as measurement light and has an expanded beam, is regulated by means of the objective lens R to have parallel rays, and is then subjected to linear polarization performed by means of the polarization plate B2. At this time, the polarization plane of the measurement light becomes coincident with the first near-infrared interferable light as described above. When the beam of measurement light reaches the beam splitter 21, the greater portion thereof is reflected toward the light detection section 3. Meanwhile, the second near-infrared interferable light beam having reached the movable mirror 22 is reflected by the mirror 22, whereby it reaches the beam splitter 21 as reference light. The greater portion of the reference light propagates toward the light detection section 3. At this time, the polarization plane of the reference light is maintained to coincide with that of the second near-infrared interferable light as described above. Accordingly, the polarization plane of the measurement light coincides with that of the reference plane.

The measurement light reflected by the beam splitter 21 and the reference light having passed through the beam splitter 21 reach the light detection section 3 in a mutually interfered condition. Here, the case where the measurement light and the reference light interfere with each other will be described. If the distance L1 between the beam splitter 21 and the eyeground and the distance L2 between the beam splitter 21 and the movable mirror 22 are approximately equal to each other, the measurement light and the reference light interfere over a distance (e.g., about 5 μm to 20 μm) corresponding to their coherence length. Thus, the light detection section 3 detects the mutually interfered near-infrared interferable light beams; i.e., interference light. Meanwhile, if the distance L1 and the distance L2 differ from each other, the measurement light and the reference light do not interfere. Thus, the measurement light and the reference light both attenuate, and the detection section 3 does not detect interference light.

In other words, when the distance L1 between the beam splitter 21 and the eyeground and the distance L2 between the beam splitter 21 and the movable mirror 22 are equal to each other, the interference light produced by the measurement light reflected at the eyeground is well detected by the light detection section 3; and when the distance L1 and the distance L2 differ from each other, the interference light is not detected by the light detection section 3. Therefore, in a state where a measurement light ray from a position different from the position of the eyeground along the profile (sectional) direction, which is defined by the distance L1, reaches the light detection section 3 because of reflection at the surface of the eyeground or the interior of the eyeground with respect to the profile direction thereof, only a measurement light ray from the position of the eyeground whose distance is equal to the distance L2 is detected as interference light produced as a result of interference with the reference light.

Since the movable mirror 22 can be moved along the optical axis of the reference light by means of the mirror-moving mechanism 23, the distance L2 can be changed freely. Therefore, the distance L1 of propagation of the measurement light which can be detected by the light detection section 3 can be changed gradually by operating the mirror-moving mechanism 23 to thereby change the distance L2. Accordingly, it becomes possible to successively change the specific region of the eyeground; i.e., the region to be measured, by gradually changing the distance L2, to thereby selectively detect interference light including the measurement light from the region to be measured.

In the light detection section 3, the light-receiving unit 31 receives the interference light in accordance with the specific wavelengths of the near-infrared interferable light beam emitted from the light emission section 1, and outputs to the AD converter 32, in a time series fashion, an electrical detection signal corresponding to the measurement light contained in the received interference light. Notably, the magnitude of the electrical detection signal is in proportion to the reflection strength of the first near-infrared interferable light beam at the eyeground; i.e., the quantity of the measurement light. The duration of the electrical detection signal can be shortened by reducing the pulse width of the near-infrared interferable light beam generated by the light source 12 of each light generator 10, whereby the distance resolution of the measurement can be improved. The AD converter 32 converts the output electrical detection signal to a digital signal, and outputs the digital signal to the computation unit 33.

On the basis of the detection signal supplied from the AD converter 32, the computation unit 33 calculates, as biological information regarding the living organism, the profile (cross sectional shape) of the eyeground, and the oxygen saturation $SO_2$ of blood flowing through a capillary vessel present at a portion corresponding to the profile. Hereinafter, this calculation will be described.

First, the computation unit 33 calculates a profile of the eyeground on the basis of the detection signal corresponding to the near-infrared interferable light beam of 830 nm output from the light emission section 1, and outputs a profile signal representing the calculated profile. Specifically, as described above, the mirror-moving mechanism 23 operates in accordance with an instruction output from the controller 4 as described above, whereby the movable mirror 22 is moved along the optical axis of the reference light so as to properly change the distance L2. Since the distance L1 is also changed as a result of the change in the distance L2, the region to be measured can be changed from the surface of the eyeground to the interior of the eyeground in the profile direction.

When the region to be measured is changed in the above-described manner, the interference light; i.e., the measurement light which reaches the light-receiving unit 31 of the light detection section 3, is measurement light reflected by a reflection surface located at a certain point in the profile direction of the eyeground, and the detection signal supplied from the light-receiving unit 31 to the computation unit 33 via the AD converter 32 represents the two-dimensional quantity distribution of the measurement light at the reflection surface. Therefore, the computation unit 33 can obtain the quantity distribution of the measurement light at each of different reflection surfaces, by changing the distance L2 between the beam splitter 21 and the movable mirror 22; i.e., the distance L1 between the beam splitter 21 and the eyeground. The quantity distribution of the measurement light changes depending on the shape of each reflection surface. Therefore, the profile of the eyeground can be calculated through execution of composing calculation in which the quantity distributions are superimposed in the profile direction. The computation unit 33 then outputs to the display section 5 the profile signal representing the calculated profile of the eyeground.

Moreover, through use of the respective detection signals (detected light quantities) supplied from the AD converter 32 and corresponding to the 780 nm component and the 830 nm component of the measurement light supplied from the AD converter 32 and the quantities of the 780 nm component and the 830 nm component of the near-infrared interferable light beam emitted from the light emission section 1, the computation unit 33 calculates the oxygen saturation $SO_2$ of a region corresponding to the calculated profile of the eyeground, and outputs an oxygen saturation signal representing the calculated oxygen saturation $SO_2$. This calculation of the oxygen saturation $SO_2$ will be described below.

The absorption of near infrared light by hemoglobin in the blood; specifically, by hemoglobin bound to oxygen (hereinafter referred to as "oxyhemoglobin") and hemoglobin not bound to oxygen (hereinafter referred to as "deoxyhemoglobin") can be represented by the following Eq. 1 in accordance with the Lambert-Beer law, as is generally known and described in literature (e.g., Hitachi Medical Corp., MEDIX, vol. 29).

$$-\ln(R(\lambda)/Ro(\lambda)) = \epsilon oxy(\lambda) \cdot Coxy \cdot d + \epsilon deoxy(\lambda) \cdot Cdeoxy \cdot d + \alpha(\lambda) + S(\lambda) \qquad \text{Eq. 1}$$

Figure 7:
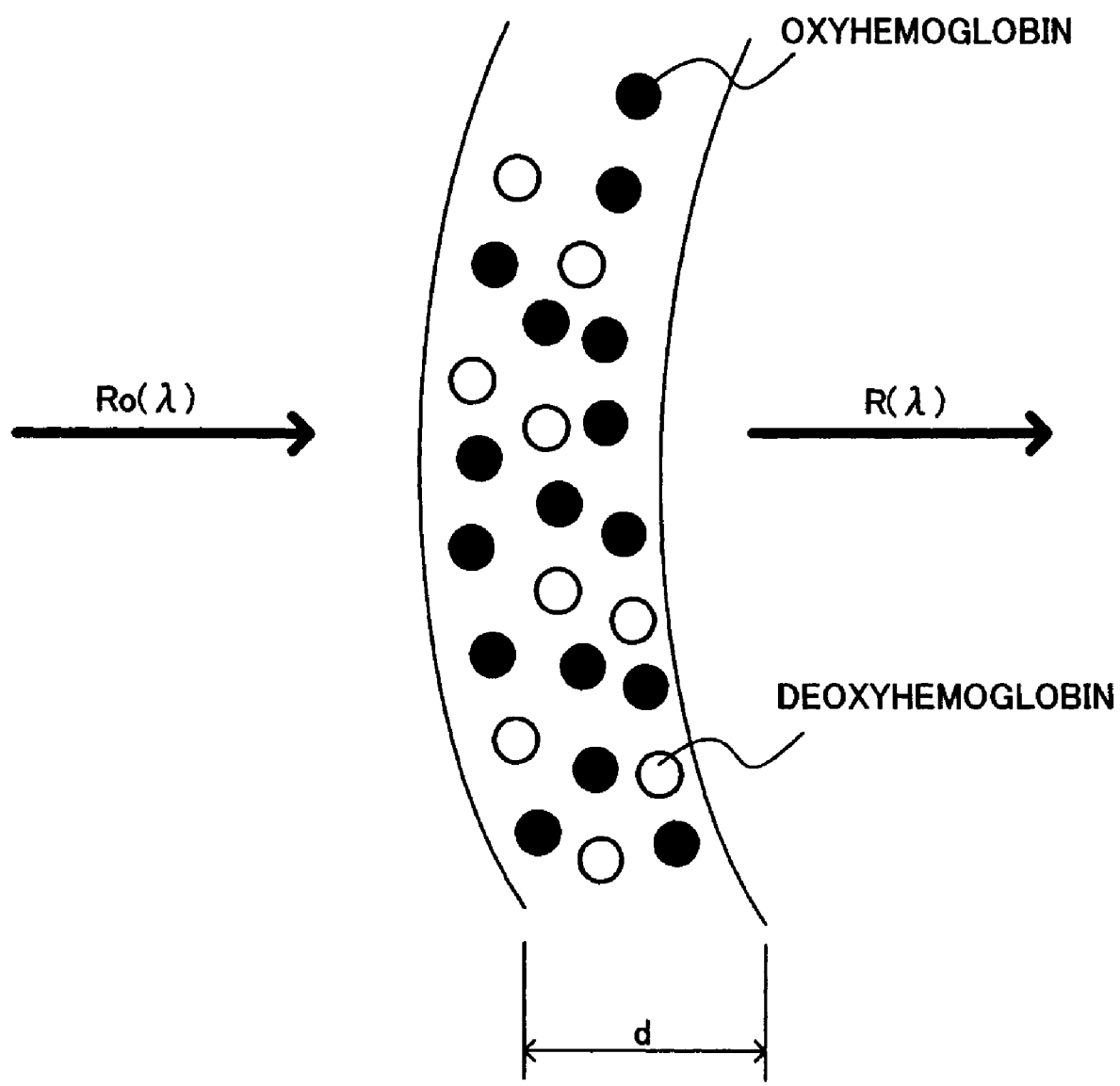
FIG. 7 is a schematic illustration used for describing a method of obtaining the degree of oxygen saturation.

As schematically shown in FIG. 7, $R(\lambda)$, $Ro(\lambda)$, and d in Eq. 1 represent the quantity of detected light of wavelength $\lambda$, the quantity of output light of wavelength $\lambda$, and the optical path length of the detected region, respectively. Further, $\epsilon oxy(\lambda)$ in Eq. 1 represents the molecular light absorption coefficient of oxyhemoglobin for the wavelength $\lambda$, and $\epsilon deoxy(\lambda)$ represents the molecular light absorption coefficient of deoxyhemoglobin for the wavelength $\lambda$. Further, Coxy in Eq. 1 represents the concentration of oxyhemoglobin, and Cdeoxy represents the concentration of deoxyhemoglobin. Moreover, $\alpha(\lambda)$ in Eq. 1 represents attenuation through absorption of light by pigments within the blood other than hemoglobin (e.g., cytochrome aa33 reflecting the demand and supply of oxygen at mitochondria in cells), and $S(\lambda)$ represents attenuation through scattering of light at the tissue of the living organism.

On the basis of the light absorption characteristics of hemoglobin in the blood represented by Eq. 1, the blood oxygen saturation $SO_2$ can be calculated in consideration of a difference between the characteristics before and after the blood flow within the blood vessel changes. Specifically, when the light absorption characteristics before a change in the blood flow are represented in accordance with Eq. 1 for a capillary present at the eyeground, the light absorption characteristics after the change in the blood flow can be represented by the following Eq. 2.

$$-\ln(\text{growth}R(\lambda)/Ro(\lambda)) = \epsilon oxy(\lambda) \cdot \text{growth}Coxy \cdot d + \epsilon deoxy(\lambda) \cdot \text{growth}Cdeoxy \cdot d + \text{growth}\alpha(\lambda) + S(\lambda) \quad \text{Eq. 2}$$

Notably, growth$R(\lambda)$, growthCoxy, growthCdeoxy, and growth$\alpha(\lambda)$ in Eq. 2 represent respective values which have increased or decreased as a result of the blood flow change; i.e., represent the quantity of detected light after the blood flow change, the concentration of oxyhemoglobin after the blood flow change, the concentration of deoxyhemoglobin after the blood flow change, and the attenuation after the blood flow change through absorption of light by pigments within the blood other than hemoglobin.

Since the quantity of light absorbed by hemoglobin within the blood is considerably large as compared with the quantity of light absorbed by pigments other than hemoglobin, $\alpha(\lambda)$ in Eq. 1 can be replaced with growth$\alpha(\lambda)$. Thus, the following Eq. 3 can be obtained by subtracting Eq. 1 from Eq. 2.

$$-\ln(\text{growth}R(\lambda)/R(\lambda)) = \epsilon oxy(\lambda) \cdot \Delta Coxy + \epsilon deoxy(\lambda) \cdot \Delta Cdeoxy \quad \text{Eq. 3}$$

Here, $\Delta Coxy$ and $\Delta Cdeoxy$ in Eq. 3 are represented by the following Eqs. 4 and 5, respectively.

$$\Delta Coxy = (\text{growth}Coxy - Coxy) \cdot d \quad \text{Eq. 4}$$

$$\Delta Cdeoxy = (\text{growth}Cdeoxy - Cdeoxy) \cdot d \quad \text{Eq. 5}$$

Figure 8:
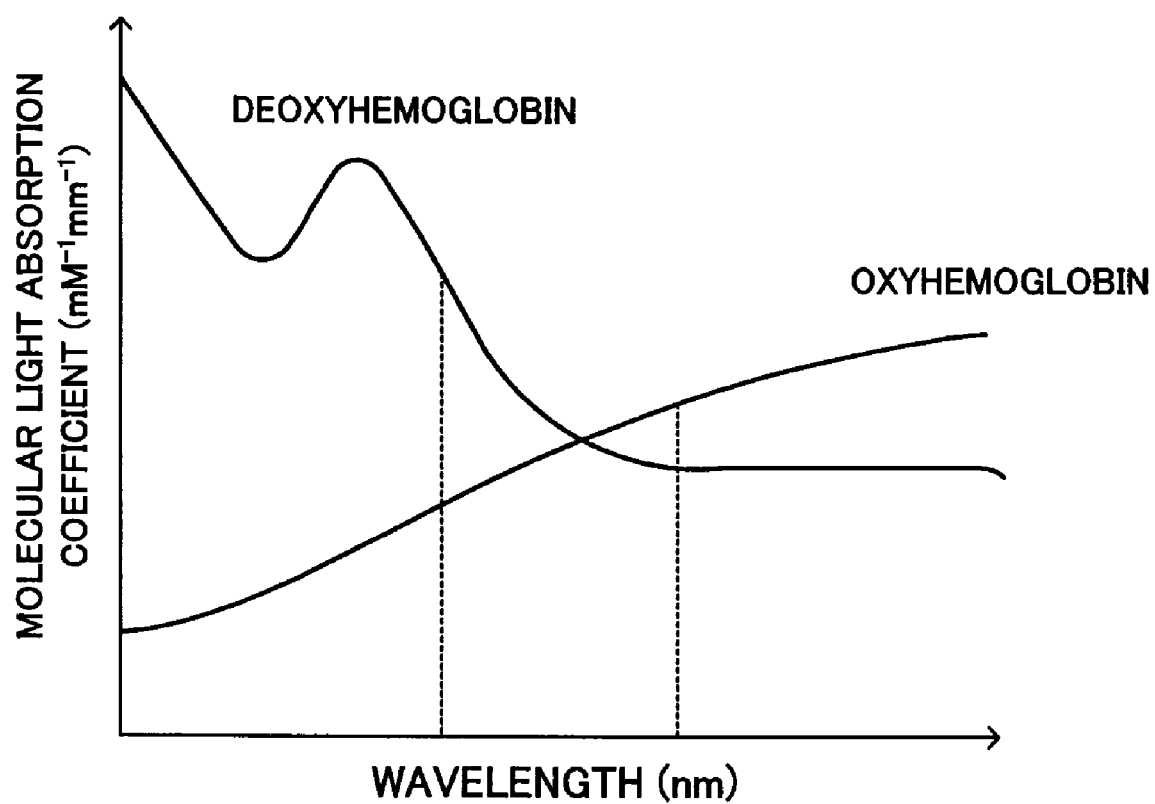
FIG. 8 is a graph schematically showing change in the molecular light absorption coefficient of oxyhemoglobin or deoxyhemoglobin with respect to wavelength.

FIG. 8 schematically shows the light absorption spectrum of hemoglobin. As shown in FIG. 8, a specific wavelength at which the oxyhemoglobin and the deoxyhemoglobin exhibit different light absorption characteristics to thereby provide a high contrast ratio; e.g., wavelengths ($\lambda$) of 780 nm and 830 nm are selected for measurement by use of near infrared interferable light. By solving Eq. 3 on the basis of results of the measurement, the oxyhemoglobin concentration change $\Delta Coxy$, the deoxyhemoglobin concentration change $\Delta Cdeoxy$, and the total hemoglobin concentration change ($\Delta Coxy + \Delta Cdeoxy$) can be calculated in a relative manner. Through calculation of these values, the relative oxygen saturation $SO_2$ represented by the following Eq. 6 can be obtained.

$$SO_2 = \Delta Coxy/(\Delta Coxy + \Delta Cdeoxy) \quad \text{Eq. 6}$$

The oxyhemoglobin concentration change $\Delta Coxy$, the deoxyhemoglobin concentration change $\Delta Cdeoxy$, the total hemoglobin concentration change ($\Delta Coxy + \Delta Cdeoxy$), and the oxygen saturation $SO_2$ are calculated by use of the detected light quantity of the interference light (more specifically, the measurement light); i.e., the first near infrared interferable light having reached the interior of the eyeground, reflected by hemoglobin within capillaries, and detected by the light detection section 3. Whereas the detected light quantity of the measurement light represents the reflection strength (change in refractive index, etc.) at a predetermined measurement depth, the measurement light is influenced by the hemoglobin concentration over the entire optical path through which the near infrared interferable light passes. That is, when the measurement depth from the surface of the eyeground is represented by D, the light quantity of the measurement light is influenced by absorption which occurs two times; i.e., absorption in the forward propagation from the eyeground surface to the measurement depth D and the back propagation from the measurement depth D to the eyeground surface.

Accordingly, the oxyhemoglobin concentration change $\Delta Coxy$, the deoxyhemoglobin concentration change $\Delta Cdeoxy$, the total hemoglobin concentration change ($\Delta Coxy + \Delta Cdeoxy$), and the oxygen saturation $SO_2$ in consideration of absorption of the measurement light inside the eyeground are preferably calculated through obtainment of the ratio between the quantity of the measurement light (interference light) at the predetermined measurement depth and the quantity of the measurement light at a point deviated from the predetermined measurement depth by a change amount $\Delta$. At this time, the light quantity ratio is preferably obtained for a pair of near infrared interferable light beams of different wavelengths (e.g., 780 nm and 830 nm), which are substantially identical in terms of the reflection strength at the predetermined measurement depth and the reflection strength at the deviated point and which differ in terms of absorption attenuation by hemoglobin. When such a pair of near infrared interferable light beams of different wavelengths is used, the refractive index, which determines the reflection strength, can be ignored within the substances which form the living organism, because of the small difference between the two wavelengths. Thus, the absorption attenuation ratio at the two wavelengths of the measurement light within the width $\Delta$ can be obtained, whereby the respective hemoglobin concentrations can be calculated by use of the absorption attenuation ratio. Accordingly, the oxyhemoglobin concentration change $\Delta Coxy$, the deoxyhemoglobin concentration change $\Delta Cdeoxy$, the total hemoglobin concentration change ($\Delta Coxy + \Delta Cdeoxy$), and the oxygen saturation $SO_2$ only at the measurement depth can be calculated.

As described above, the computation unit 33 calculates the oxygen saturation $SO_2$ in accordance with the above-described Eqs. 1 to 6 and through use of the obtained detected signals corresponding to the near infrared interferable light beams of 830 nm and 780 nm; i.e., the light quantity distribution at a certain reflection surface as in the case of the above-described calculation of the profile of the eyeground. Accordingly, through execution of composing calculation in which the oxygen saturations $SO_2$ calculated for successively selected reflection surfaces are superimposed in the profile direction, the oxygen saturation $SO_2$ corresponding to each position of the profile of the eyeground can be calculated. The computation unit 33 then outputs to the display section 5 the oxygen saturation signal representing the calculated oxygen saturation $SO_2$.

In the display section 5, the frame control circuit 51a of the image-processing unit 51 causes the frame memories 51b to temporarily store the profile signal and the oxygen saturation signal output from the computation unit 33 of the light detection section 3. Subsequently, the frame control circuit 51a causes the multiplexer 51c to output to the image generation circuit 51d the profile signal and the oxygen saturation signal and temporarily stored at predetermined memory locations of the frame memories 51b. The image generation circuit 51d generates, on the basis of the output profile signal, profile image data representing the profile of the eyeground, and generates, on the basis of the output oxygen saturation signal, oxygen saturation image data representing the oxygen saturation $SO_2$ corresponding to each position of the profile of the eyeground. The image generation circuit 51*d* then outputs the generated profile image data and oxygen saturation image data to the display image data storing circuit 52.

The display image data storing circuit 52 temporarily stores the profile image data and oxygen saturation image data supplied from the image generation circuit 51*d*. The conversion circuit 53 converts the image data stored in the display image data storing circuit 52 to display data, and the monitor 54 displays the profile of the eyeground and the oxygen saturation of the eyeground individually or in a composed or mixed manner.

As can be understood from the above description, the optical interference apparatus H according to the present embodiment can use quite efficiently the near infrared interferable light beam emitted from the light emission section 1, and can enhance the measurement accuracy. Further, since the beam splitter 21 of the light interference section does not polarize the near infrared interferable light beam received from the light emission section 1, provision of a ¼ λ plate is not required. Therefore, the dependency on the wavelength of the near infrared interferable light beam emitted from the light source 12 can be eliminated, whereby the structure of the optical system of the optical interference apparatus H can be simplified, and operations necessary for measurement, such as setting of the optical axis can be performed quite easily.

When the light detection section 3 receives the interference light from the beam splitter 21, the computation unit 33 can calculate the profile shape and the oxygen saturation $SO_2$ on the basis of the quantity of light received by the light-receiving unit 31. Thus, the display section 5 can display the calculated profile shape and the oxygen saturation $SO_2$ in a visible manner. Accordingly, a larger number of pieces of accurate information can be provided to a medical doctor or the like.

In the first embodiment, the controller 4 supplies to the two light generators 10 of the light emission section 1 drive signals for driving the light generators 10 at predetermined, short intervals. However, the controller 4 may be configured to supply the drive signals such that the output intervals of near infrared interferable light by the light generators 10 become longer. Through an increase in the output intervals of near infrared interferable light, for example, the light detection speed of the light-receiving unit 31 (photo detector, etc.) can be decreased, so that the production cost of the optical interference apparatus H can be lowered.

b. Second Embodiment

In the first embodiment, the controller 4 controls the light emission section 1 such that a predetermined, short interval is present between the light emission timings of the two light generators 10, and the light generators 10 emit near infrared interferable light in the form of pulses. The light emission timings can be made coincident with each other by means of spread-spectrum-modulation of the near infrared interferable light output from the light generators 10. Hereinafter, this second embodiment will be described, wherein portions identical with those of the first embodiment are denoted by the same reference numerals, and their detailed descriptions are not repeated.

Figure 9:
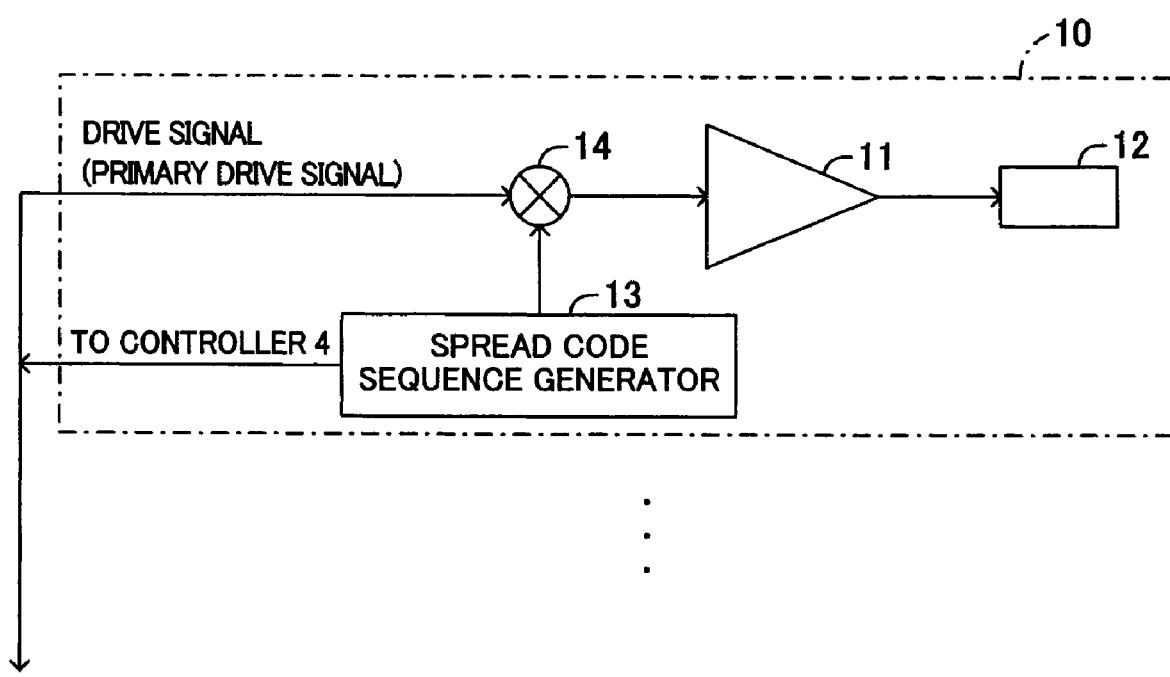
FIG. 9 is a block diagram schematically showing the configuration of a light emission section according to a second embodiment of the present invention.

The light emission section 1 of the optical interference apparatus H of the second embodiment outputs near infrared interferable light beams having specific wavelengths and having undergone spread-spectrum-modulation. Therefore, as shown in FIG. 9, each of the light generators 10 of the second embodiment includes a spread code sequence generator 13 for generating a spread code sequence such as a 128-bit pseudorandom noise (PN) sequence which consists of "+1" and "−1." The spread code sequence generator 13 generates, for example, a Hadamard sequence, an M sequence, or a Gold code sequence as a PN sequence.

The aforementioned Hadamard sequence, M sequence, and Gold code sequence are similar to those employed for spread spectrum modulation, and thus detailed description of their generation methods is omitted. However, these sequences will next be described briefly. The Hadamard sequence is obtained from each of the rows or columns of a Hadamard matrix which consists of "+1" and "−1." The M sequence is a binary sequence obtained by use of a shift register consisting of n 1-bit register units, each memorizing "0" or "+1." The shift register is configured such that the exclusive logical sum of the value of an intermediate register unit and the value of the final register unit is fed to the first register unit. Notably, in order to transform this binary sequence into a PN sequence, the value "0" is converted into "−1" through level conversion. The Gold code sequence is basically obtained through addition of two types of M sequences. Therefore, the Gold code sequence can increase the number of sequences considerably, as compared with the case of the M sequence. Among these sequences serving as PN sequences, two arbitrary sequences are orthogonal with each other, and the sum of products of the two sequences yields the value "0." That is, one of these sequences has zero correlation with the other sequences.

The PN sequence generated by the spread code sequence generator 13 is output to the controller 4, and is also output to a multiplier 14. The multiplier 14 multiplies a drive signal (primary drive signal) supplied from the controller 4 by the PN sequence supplied from the spread code sequence generator 13. Thus, the drive signal (primary drive signal) can be subjected to spread spectrum modulation. Notably, various modulation schemes can be employed so as to modulate the drive signal (primary drive signal). For example, ASK (Amplitude Shift Keying) modulation, FSK (Frequency Shift Keying) modulation, PSK (Phase Shift Keying) modulation, or the like can be used. The multiplier 14 supplies the thus-spread-spectrum-modulated drive signal (i.e., secondary drive signal) to a light source driver 11. The multiplier 14 serves as the spread spectrum modulation means of the apparatus of the present invention. The light source driver 11 of the second embodiment drives the light source 12 on the basis of the secondary drive signal supplied from the multiplier 14.

Figure 10:
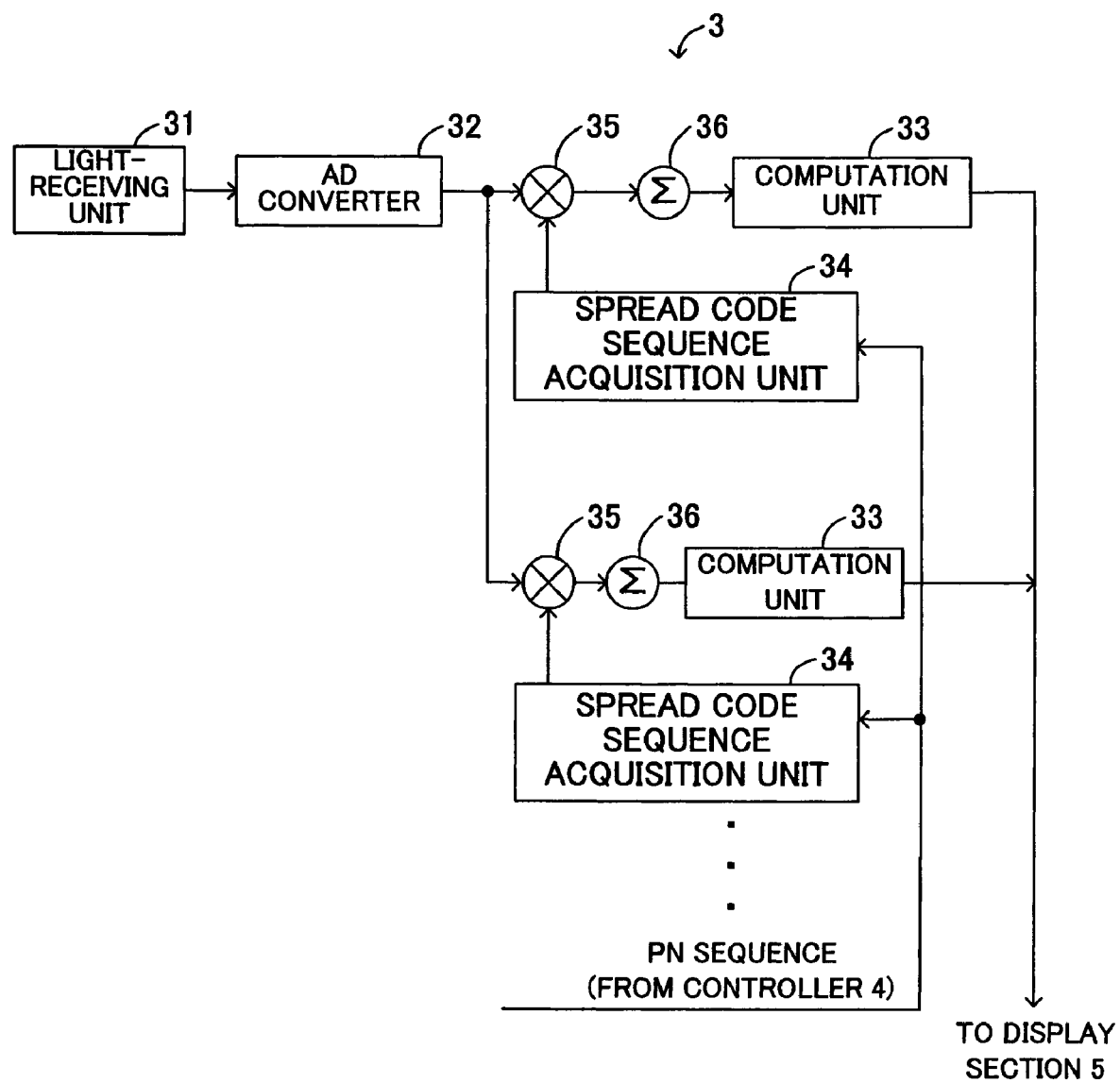
FIG. 10 is a block diagram schematically showing the configuration of a light detection section according to the second embodiment.

As shown in FIG. 10, the light detection section 3 of the second embodiment includes a plurality of spread code sequence acquisition units 34 for selectively receiving the measurement light (interfered with the reference light) derived from the near infrared interferable light beam emitted from a specific light generator 10 of the light emission section 1. As indicated by a broken line in FIG. 1, each spread code sequence acquisition unit 34 is connected to the controller 4, and acquires, from the controller 4, the spread code sequence (i.e., PN sequence) contained in the near infrared interferable light beam emitted from the corresponding specific light generator 10. The spread code sequence acquisition unit 34 supplies the thus-acquired PN sequence to a corresponding multiplier 35.

The multiplier 35 multiplies the detection signal output from the AD converter 32 by the PN sequence supplied from the spread code sequence acquisition unit 34. Subsequently, the multiplier 35 outputs the thus-calculated product of the detection signal and the PN sequence to an accumulator 36. The accumulator 36 accumulates the thus-supplied product over one or more periods of the above-supplied PN sequence.

Subsequently, the accumulator 36 outputs, to the computation unit 33, a detection signal corresponding to the measurement light; i.e., near infrared interferable light which has been emitted from the specific light generator 10 and reflected at the eyeground.

Next, operation of the optical interference apparatus H of the second embodiment having the above-described configuration will be described, while observation of the eyeground of a patient is taken as an example as in the above-described first embodiment.

In the second embodiment as well, a medical doctor or operator places the optical interference apparatus H such that the eyeball of the patient is located on the optical axis of the near infrared interferable light beam output from the light emission section 1. The medical doctor or operator then operates the controller 4 to thereby instruct start of output of the near infrared interferable light beam. In response thereto, the controller 4 supplies to the two light generators 10 of the light emission section 1 respective primary drive signals for driving the light generators 10. In response thereto, the two light generators 10 simultaneously start their operations and output a near infrared interferable light beam of 780 nm and a near infrared interferable light beam of 830 nm, respectively.

That is, in each of the light generators 10, the spread code sequence generator 13 generates, for example, a Gold code sequence as a PN sequence. Subsequently, the spread code sequence generator 13 outputs the thus-generated PN sequence to the controller 4, as well as to the multiplier 14. The multiplier 14 calculates the product of the PN sequence and the drive signal supplied from the controller 4 (i.e., primary drive signal), thereby subjecting the drive signal to spread spectrum modulation. When the thus-spread-spectrum-modulated drive signal (i.e., secondary drive signal) is supplied to the light source driver 11, the light source driver 11 causes the light source 12 to generate an optical pulse.

The two near infrared interferable light beams output from the light emission section 1 are optically mixed by means of the half mirror. Subsequently, like the first embodiment, the resultant light beam is optically divided into two near infrared interferable light beams by means of the beam splitter 21 of the light interfering section 2. The first near infrared interferable light beam propagates straight and reaches the eyeball of the patient, and the second near infrared interferable light beam reaches the movable mirror 22. The measurement light reflected at the eyeground and the reference light reflected by the movable mirror 22 interfere with each other and reach the light detection section 3.

Next, detection of the interference light; i.e., the measurement light, by the light detection section 3 will be described. The measurement light having interfered with the reference light at the beam splitter 21 is detected by the light-receiving unit 31 of the light detection section 3. At this time, both a light ray having a wavelength of 780 nm and a light ray having a wavelength of 830 nm reach the light-receiving unit 31 as the measurement light. In this condition, the controller 4 controls the light detection section 3 to selectively detect, among the received measurement light rays, a measurement light ray which is based on the near infrared interferable light beam emitted from the specific light generator 10. The control by the controller 4 will be described specifically.

After having supplied the primary drive signals to the light emission section 1 as described above, the controller 4 acquires PN sequences from the light generators 10. Subsequently, the controller 4 supplies, to the light detection section 3, the PN sequences acquired from the spread code sequence generators 13 of the light generators 10. Thus, the spread code sequence acquisition units 34 of the light detection section 3 acquire the supplied PN sequences, and supply the thus-acquired PN sequences to the multipliers 35.

The light-receiving unit 31 receives all the measurement light rays having interfered with the reference light rays at the beam splitter 21, and outputs, to the AD converter 32, electrical detection signals corresponding to the thus-received measurement light rays in a time-series manner. The AD converter 32 converts the thus-output electrical detection signals into digital signals, and outputs the thus-digitized detection signals to the multipliers 35.

In this state, each of the multipliers 35 calculates the product of the digital detection signal output from the AD converter 32 and the PN sequence supplied from the corresponding spread code sequence acquisition unit 34. Subsequently, the multiplier 35 outputs the thus-calculated product to the corresponding accumulator 36, and the accumulator 36 accumulates the thus-output product over one period (i.e., 128 bit length) or more of the PN sequence. Thus, through the processing for obtaining the sum of products performed by the multipliers 35 and the accumulators 36, the digital detection signals can be correlated with the above-supplied PN sequences, whereby only a detection signal corresponding to the near infrared interferable light beam from the specific light generator 10; specifically, a detection signal corresponding to the measurement light ray having a wavelength of 780 nm or 830 nm, is selected and output.

As described above, two different PN sequences are orthogonal with each other; i.e., the product of the different PN sequences becomes "0." Therefore, when, for example, a spread code sequence acquisition unit 34 supplies the PN sequence of a specific light generator 10 to the corresponding multiplier 35, the product of the supplied PN sequence and a detection signal (among the detection signals output from the AD converter 32) other than the detection signal corresponding to the near infrared interferable light beam output from the specific light generator 10 becomes "0." Therefore, the value obtained through accumulation by the accumulator 36 over at least one period of the PN sequence becomes "0," and the correlation becomes "0." Thus, a detection signal which does not have the PN sequence supplied from the spread code sequence acquisition unit 34 (or a detection signal which does not match the PN sequence); i.e., the measurement light ray derived from the near infrared interferable light beam output from a light generator other than the specific light generator 10 is selectively eliminated; and only the detection signal corresponding to the measurement light ray derived from the near infrared interferable light beam output from the specific light generator 10 is output to the computation unit 33.

In the second embodiment as well, the movable mirror 22 is moved so as to gradually change the position of the reflection surface of the measurement light in the profile direction of the eyeground. Through this operation, as in the first embodiment, the computation unit 33 calculates the profile of the eyeground by use of the quantity distribution of the measurement light at the reflection surface, and outputs to the display section 5 a profile signal representing the calculated profile of the eyeground. Moreover, as in the first embodiment, through use of the selectively obtained detection signals corresponding to the near infrared interferable light beams of 780 nm and 830 nm, the computation unit 33 calculates the oxygen saturation $SO_2$ in accordance with the above-described Eqs. 1 to 6, and outputs to the display section 5 an oxygen saturation signal representing the calculated oxygen saturation $SO_2$. Thus, as in the first embodiment, the display section 5 displays the profile of the eyeground and the oxygen saturation of the eyeground individually or in a composed or mixed manner.

As can be understood from the above description, the optical interference apparatus H according to the second embodiment has advantageous effects similar to those attained in the first embodiment. Moreover, through simultaneous emission of two near infrared interferable light beams having different wavelengths, change in oxygen saturation $SO_2$ can be calculated more exactly. That is, although change in oxygen saturation $SO_2$ with time is relatively slow, strictly speaking, it changes with time. In contrast, in the case where two near infrared interferable light beams having different wavelengths are output simultaneously, measurement light rays which reflect the oxygen saturation $SO_2$ at the same point in time reach the light detection section 3. Therefore, the oxygen saturation $SO_2$ at the instantaneous time can be well calculated, and change in the oxygen saturation $SO_2$ with elapse of time can be calculated quite accurately.

In the second embodiment, secondary drive signals are generated through spread spectrum modulation of primary drive signals; i.e., drive signals supplied from the controller 4, whereby two near infrared interferable light beams are output without interfering with each other. However, the second embodiment may be modified so as to generate the secondary drive signals through FDMA (frequency division multiple access) modulation of the primary drive signals supplied from the controller 4 to prevent the interference between the output two near infrared interferable light beams. In this case, the spread code sequence generators 13 and the multipliers 14 of the light emission section 1 of the second embodiment are removed, and an FDMA modulator is provided. Moreover, in this case, the spread code sequence acquisition units 34, the multipliers 35, and the accumulators 36 of the light detection section 3 of the second embodiment are removed, and a demodulator is provided. Notably, operation of the FDMA modulator will not be described in detail, because modulation processing and demodulation processing can be performed by use of widely known conventional methods.

In the light emission section 1 of the optical interference apparatus H configured as described above, the primary drive signals supplied from the controller 4 undergo the FDMA modulation performed by the FDMA modulator, whereby the secondary drive signals are generated. The two light sources 12 simultaneously emit two near infrared interferable light beams on the basis of the generated secondary drive signals. In the light detection section 3, the demodulator demodulates the detection signal output from the AD converter 32, whereby only the detection signal corresponding to the measurement light ray derived from the near infrared interferable light beam output from the specific light generator 10 is output to the computation unit 33. Accordingly, in this case as well, effects similar to those attained in the second embodiment are expected.

The present invention is not limited to the above-described embodiments, and various modifications are possible without departing from the scope of the present invention.

For example, in the above-described embodiments, oxygen saturation $SO_2$ is calculated in accordance with the above-described Eqs. 1 to 6 (more specifically, Eq. 6). As is apparent from Eqs. 4 and 5, the oxyhemoglobin concentration change $\Delta Coxy$ and the deoxyhemoglobin concentration change $\Delta Cdeoxy$ calculated in the embodiments change depending on the optical path length d. In general, precise measurement or calculation of the optical path length d of light having entered the interior of a living organism is considerably difficult. Accordingly, the optical path length d in Eqs. 4 and 5 is a relative value, and oxygen saturation $SO_2$ calculated in accordance with Eq. 6 by use of the oxyhemoglobin concentration change $\Delta Coxy$ and the deoxyhemoglobin concentration change $\Delta Cdeoxy$ is also a relative value.

In contrast, in the case where oxygen saturation $SO_2$ is calculated in accordance with the following equations, the oxygen saturation $SO_2$ in the arterial system; i.e., the oxygen saturation $SO_2$ in the artery or arteriole, is calculated. Since this oxygen saturation calculation method is widely known as disclosed in, for example, Japanese Patent Application Laid-Open (kokai) No. S63-111837, its detailed description is omitted.

Extinction of infrared light within a living organism can be calculated by the following Eq. 7

$$-\log(I1/I0) = E \cdot C \cdot e + A \qquad \text{Eq. 7}$$

In Eq. 7, I1 represents the quantity of transmitted light, and I0 represents the quantity of incident light. Further, E represents the light absorption coefficient of hemoglobin, C represents the concentration of hemoglobin in the blood, e represents the thickness of a blood layer (corresponding to the optical path length d in Eqs. 4 and 5), and A represents the light extinction of the tissue layer. Although Eq. 7 is adapted to calculate the extinction of infrared light having passed through the interior of a living organism, even reflected infrared light is known to exhibit similar characteristics.

If the thickness e of a blood layer changes by $\Delta e$ due to pulsation, a change in infrared light extinction can be calculated in accordance with the following Eq. 8.

$$-\log((I1/I0) - \log(I2/I0)) = E \cdot C \cdot e - E \cdot C \cdot (e - \Delta e) \qquad \text{Eq. 8}$$

Eq. 8 can be simplified to the following Eq. 9

$$-\log(I2/I1) = E \cdot C \cdot \Delta e \qquad \text{Eq. 9}$$

I2 in Eqs. 8 and 9 represents the quantity of transmitted light after the thickness of the blood layer has changed.

Next, there will be considered the case where an infrared light beam having a wavelength $\lambda 1$ and an infrared light beam having a wavelength $\lambda 2$ have passed the interior of a living organism with resultant generation of a first transmitted light beam ($\lambda 1$) of quantity I1 and a second transmitted light beam ($\lambda 2$) of quantity I2. When the quantity of the first transmitted light beam ($\lambda 1$) as measured at times t1 and t2 is represented by I11 and I21, and the quantity of the second transmitted light beam ($\lambda 2$) as measured at times t1 and t2 is represented by I12 and I22, the change in infrared light extinction at times t1 and t2 can be represented by the following Eqs. 10 and 11, which are based on Eq. 9.

$$-\log(I21/I11) = E1 \cdot C \cdot \Delta e \qquad \text{Eq. 10}$$

$$-\log(I22/I12) = E2 \cdot C \cdot \Delta e \qquad \text{Eq. 11}$$

E1 in Eq. 10 represents the light absorption coefficient of hemoglobin for the infrared light beam of $\lambda 1$, and E2 in Eq. 11 represents the light absorption coefficient of hemoglobin for the infrared light beam of $\lambda 2$. When the term $\Delta e$, which represents change in the thickness of the blood layer, is eliminated by dividing Eq. 11 by Eq. 10, the following Eq. 12 is obtained.

$$\log(I12/I22)/\log(I11/I21) = E2/E1 \qquad \text{Eq. 12}$$

Therefore, the following Eq. 13 is obtained through modification of Eq. 12.

$$E2 = E1 \cdot \log(I12/I22)/\log(I11/I21) \qquad \text{Eq. 13}$$

Figure 11:
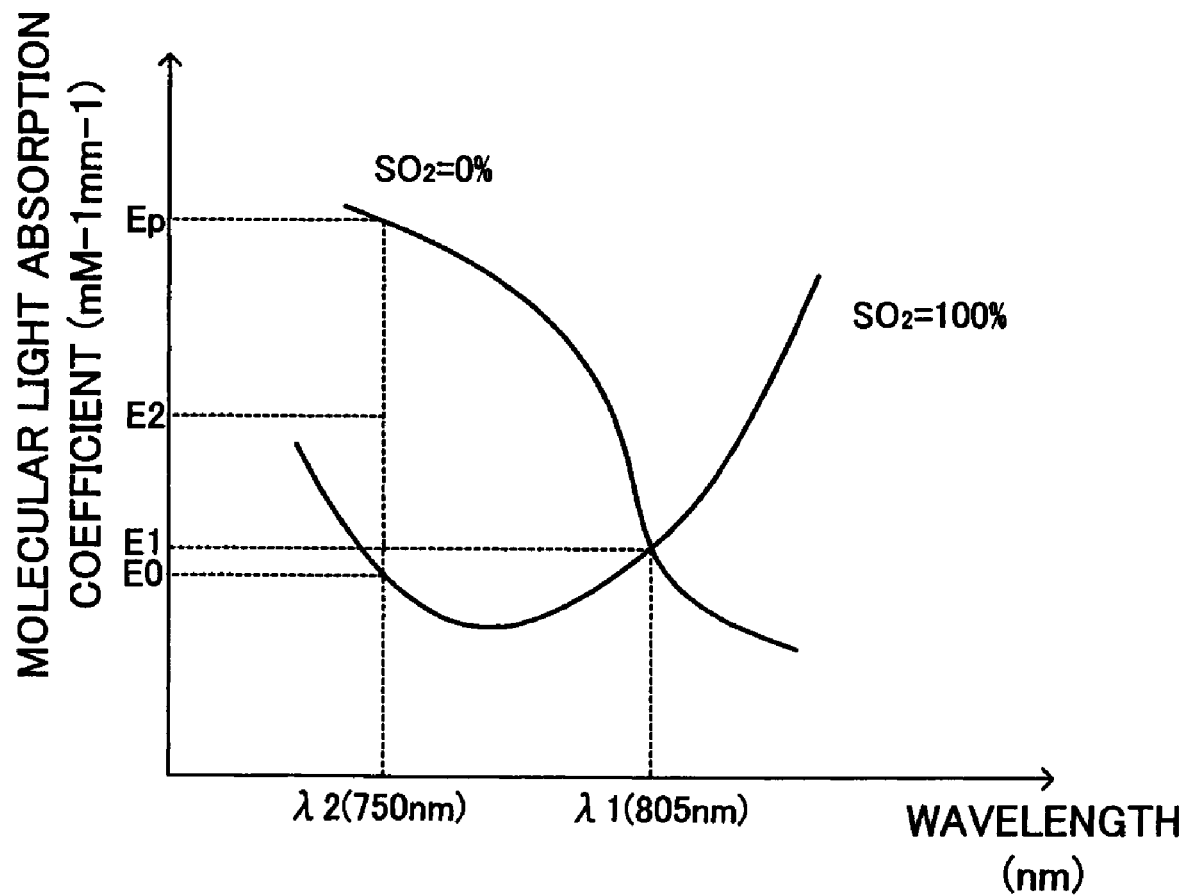
FIG. 11 is a graph relating to a modified embodiment of the present invention and schematically showing change in molecular light absorption coefficient with respect to wavelength for different degrees of oxygen saturation.

FIG. 11 shows change in light absorption spectrum of hemoglobin with oxygen saturation. Here, 805 nm is selected as a light absorption wavelength corresponding to the light absorption coefficient E1 of hemoglobin. Thus, the intersection between a curve for $SO_2=0\%$ and a curve for $SO_2=100\%$ is obtained. As a result, the light absorption coefficient E1 becomes a value which is not influenced by oxygen saturation. Further, for example, 750 nm is selected as a light absorption wavelength corresponding to the light absorption coefficient E2 of hemoglobin, the light absorption coefficient of hemoglobin at the time when oxygen saturation $SO_2=0\%$ is represented by Ep, and the light absorption coefficient of hemoglobin at the time when oxygen saturation $SO_2=100\%$ is represented by E0, the present oxygen saturation $SO_2$ can be calculated in accordance with the following Eq. 14.

$$SO_2=(E2-Ep)/(E0-Ep) \qquad \text{Eq. 14}$$

Since the oxygen saturation $SO_2$ calculated in accordance with Eq. 14 is calculated without use of any relative value, the actual oxygen saturation can be obtained. Accordingly, in diagnosis by a medical doctor, more accurate oxygen saturation $SO_2$ can be provided. Notably, since the thickness of the blood layer changes at considerably high speed, in this case, preferably, the light sources 12 of the light generator 10 are simultaneously driven so as to simultaneously output near infrared interferable light beams having different specific wavelengths, as described in relation to the second embodiment.

In the second embodiment and its modification, the light emission section 1 is configured to drive the light sources 12 on the basis of the secondary drive signals obtained through modulation of the primary drive signals supplied from the controller 4, to thereby output near infrared interferable light beams. The light detection section 3 is configured to separate a detection signal through demodulation of the secondary drive signals contained in interference light to the primary drive signals. However, the optical interference apparatus H may be configured such that the interference light entering the light detection section 3 is optically separated by use of, for example, a dichroic mirror, so as to simultaneously output two near infrared interferable light beams having different specific wavelengths, without modulating the drive signals supplied from the controller 4. Notably, in this case, the light detection section 3 includes two light-receiving units 31.

According this structure, in the light emission section 1, the two light sources 12 simultaneously output a near infrared interferable light beam of 780 nm and a near infrared interferable light beam of 830 nm on the basis of predetermined drive signals supplied from the controller 4. The two emitted near infrared interferable light beams are optically mixed by means of the half mirror and output to the light interference section 2. As in the second embodiment, the light interference section 2 outputs toward the light detection section 3 interference light produced as a result of interference between the measurement light and the reference light. At this time, since the dichroic mirror is provided on the optical axis of the output interference light, the interference light having reached the mirror is optically divided into two light rays. That is, the dichroic mirror divides the interference light into an interference light ray having a wavelength of 780 nm and an interference light ray having a wavelength of 830 nm, which reach the two light-receiving units 31 provided in the light detection section 3.

The interference light rays having reached the light-receiving units 31 are supplied, as detection signals, to the AD converter 32, as in the second embodiment. The AD converter 32 supplies the corresponding digital detection signals to the computation unit 33, whereby, as in the second embodiment, profile and oxygen saturation $SO_2$ are calculated. Therefore, effects similar to those attained in the second embodiment are expected. Moreover, since a modulation unit and a demodulation unit are not required, the structure of the optical interference apparatus H can be simplified.

In the above-described embodiments and modifications, profile shape and oxygen saturation $SO_2$ (biological information) are calculated by use of the quantity of near infrared interferable light output from the light emission section 1 and the quantity of interference light detected by the light detection section 3. However, other types of biological information, such as blood flow within the blood vessel and change in blood flow, can be calculated and displayed at the display section 5, so long as these can be calculated by use of the quantity of near infrared interferable light output from the light emission section 1 and the quantity of interference light detected by the light detection section 3.

The optical interference apparatus H can obtain information regarding objects to be examined other than living organisms, insofar as the objects reflect light in a scattered manner. For example, a very small change in distance between objects or the surface unevenness of an object can be measured on the basis of fringes detected by the light detection section 3. In the above-described embodiments, since the object to be examined is a living organism, measurement is performed by use of a plurality of near infrared interferable light beams having specific wavelengths. However, in the case where a very small change in distance between objects or the surface unevenness of an object is measured, no limitation is imposed on the light generated by the light source 12, and light other than near infrared interferable light can be used. Further, no particular limitation is imposed on the number of the specific wavelengths used for measurement, insofar as the number of the specific wavelengths one or more. Notably, since a widely known method can be employed so as to measure a very small change in distance between objects or the surface unevenness of an object, its description will be omitted.

Depending on an object which is measured by use of the optical interference apparatus H, its scattered reflection light (i.e., measurement light) may attenuate greatly (e.g., about $10^{-1}$ to $10^{-8}$). In a state in which the measurement light attenuates, the quantity of the reference light is desirably adjusted so as to compensate the attenuation of the measurement light to thereby maintain the measurement accuracy. Therefore, as shown by a broken line in FIG. 1, a ND (Neutral Density) filter 24 is provided between the beam splitter 21 and the movable mirror 22 so as to properly reduce the quantity of the reference light. Further, a ½ λ plate corresponding to the near infrared interferable light emitted from each light source 12 is preferably disposed between the light source 12 and the half mirror so as to properly reduce the quantity of the reference light. As a result of provision of these components, the quantity of the reference light can be made equal to that of the measurement light, whereby the proper quantity of interference light can be obtained, and thus, good measurement accuracy can be maintained.

Moreover, in the above-described embodiments and their modifications, a half mirror is provided so as to cause the near infrared interferable light beams emitted from the light sources 12 to have the common axis, or mix these near infrared interferable light beams. However, in place of the half mirror, an optical coupler which includes an optical fiber or the like as a main component may be employed so as to guide the near infrared interferable light beams from the light sources 12. Through use of the optical coupler, the near infrared interferable light beams emitted from the light sources 12 can be efficiently utilized for measurement of an object to be examined.

In the first embodiment, the light sources 12 of the light emission section 1 successively generate light beams with a predetermined short time interval therebetween, on the basis of the drive signals supplied from the controller 4. Even in such a case where the light sources 12 are driven to successively generate light beams, needless to say, it is possible to generate secondary drive signals by modulating the drive signals supplied from the controller 4 (primary drive signals) and drive the light sources 12 so as to generate light beams on the basis of the secondary drive signals, as has been described in relation to the second embodiment and modifications.

What is claimed is:

1. An optical interference apparatus comprising:
    a controller operable by a user and outputting various signals on the basis of instructions from the user;
    a light emission section including a light source for emitting light on the basis of a predetermined drive signal supplied from the controller and adapted to emit a beam of light having a specific wavelength;
    a light interference section including
    splitting means having a low-reflection region for permitting the greater portion of the light beam emitted from the light emission section to pass therethrough toward an object to be examined, a portion of the emitted light beam being reflected and optically separated at the low-reflection region, reflection means for reflecting toward the splitting means the portion of the light beam reflected and separated at the low-reflection region of the splitting means,
    moving means for moving the reflection means along the optical axis of the light beam separated through reflection, and light interference means for causing optical interference between the light beam reflected by the reflection means and the light beam reflected by the object to be examined; and
    a light detection section including light-receiving means for receiving interference light produced as a result of the optical interference at the light interference section.

2. An optical interference apparatus according to claim 1, wherein the splitting means of the light interference section includes:
    a substrate formed of a transparent material,
    a reflection layer formed on one side of the substrate, and
    a transmission hole formed in the reflection layer so as to permit passage therethrough of the greater portion of the light beam emitted from the light emission section.

3. An optical interference apparatus according to claim 2, wherein the splitting means of the light interference section further includes:
    a protection layer formed on the reflection layer so as to prevent deterioration of the reflection layer, and
    a reflection suppression layer formed on the other side of the substrate and suppressing reflection of the light beam propagating from the light emission section.

4. An optical interference apparatus according to claim 1, wherein
    the light emission section includes a plurality of light sources emitting near infrared interferable light on the basis of predetermined drive signals supplied from the controller and adapted to emit near infrared interferable light beams having different specific wavelengths; and
    the light detection section includes light-receiving means for receiving interference light including the near infrared interferable light beams emitted from the light emission section and having different specific wavelengths.

5. An optical interference apparatus according to claim 4, wherein
    the light emission section further includes spread spectrum modulation means for modulating predetermined primary drive signals supplied from the controller by spread spectrum modulation to thereby generate secondary drive signals, and light-mixing means for optically mixing the near infrared interferable light beams having different specific wavelengths simultaneously emitted from the light sources driven simultaneously on the basis of the secondary drive signals; and
    the light detection section further includes demodulation means for despreading and demodulating the secondary drive signals contained in the interference light received by the light-receiving means to thereby obtain the predetermined primary drive signals.

6. An optical interference apparatus according to claim 4, wherein
    the light emission section further includes frequency-division-multiple-access-modulation means for modulating predetermined primary drive signals supplied from the controller by means of frequency division multiple-access modulation to thereby generate secondary drive signals, and light-mixing means for optically mixing the near infrared interferable light beams having different specific wavelengths simultaneously emitted from the light sources driven simultaneously on the basis of the secondary drive signals; and
    the light detection section further includes demodulation means for demodulating the secondary drive signals contained in the interference light received by the light-receiving means to thereby obtain the predetermined primary drive signals.

7. An optical interference apparatus according to claim 4, wherein the light emission section acquires predetermined drive signals supplied from the controller with a predetermined time interval therebetween, and the light sources are successively driven on the basis of the acquired predetermined drive signals so as to successively emit near infrared interferable light beams having different specific wavelengths with the predetermined time interval therebetween.

8. An optical interference apparatus according to claim 7, wherein
    the light emission section further includes spread spectrum modulation means for modulating, by spread spectrum modulation, predetermined drive signals supplied from the controller with the predetermined time interval therebetween to thereby generate modulated drive signals, whereby the light sources are successively driven by the modulated drive signals so as to successively emit near infrared interferable light beams having different specific wavelengths with the predetermined time interval therebetween; and
    the light detection section further includes demodulation means for demodulating the modulated drive signals contained in the interference light received by the light receiving means to thereby obtain the predetermined drive signals.

9. An optical interference apparatus according to claim 7, wherein
    the light emission section further includes modulation means for modulating, by means of frequency division multiple-access modulation, predetermined drive signals supplied from the controller with the predetermined time interval therebetween to thereby generate modulated drive signals, whereby the light sources are successively driven by the modulated drive signals so as to successively emit near infrared interferable light beams having different specific wavelengths with the predetermined time interval therebetween; and the light detection section further includes demodulation means for demodulating the modulated drive signals contained in the interference light received by the light receiving means to thereby obtain the predetermined drive signals.

10. An optical interference apparatus according to claim 1, further comprising a light splitting section provided between the light interference section and the light detection section so as to optically separate interference light rays produced as a result of optical interference at the light interference section, wherein the light detection section includes a plurality of right-receiving means for receiving the interference light rays separated by the light separation section.

11. An optical interference apparatus according to claim 1, wherein the light detection section further comprises calculation means for calculating predetermined information regarding the object on the basis of the light quantities of the interference light rays received by the light-receiving means.

12. An optical interference apparatus according to claim 11, further comprising a display section including image data generation means for generating visible image data on the basis of the predetermined information regarding the object calculated by the calculation means and display means for displaying an image on the basis of the image data generated by the image data generation means.

13. An optical interference apparatus according to claim 11, wherein
the object to be examined is a living organism; and
the calculation means of the light detection section includes profile information calculation means for calculating profile information representing the profile of the object on the basis of the light quantities of the interference light rays received by the light-receiving means, and biological information calculation means for calculating biological information of the object associated with metabolism of the living organism on the basis of the light quantities of the near infrared interferable light beams emitted from the light emission section and the light quantities of the interference light rays received by the light-receiving means.

14. An optical interference apparatus according to claim 13, wherein the biological information calculated by the biological information calculation means is one selected from the group consisting of blood volume, blood flow rate, change in blood flow, and the degree of oxygen saturation within a blood vessel of the living organism.

15. An optical interference apparatus according to claim 13, wherein the living organism is the eyeground of an eyeball.

* * * * *